(12) United States Patent
Knust et al.

(10) Patent No.: US 8,293,730 B2
(45) Date of Patent: Oct. 23, 2012

(54) SUBSTITUTED IMIDAZO[1,5-A][1,2,4]TRIAZOLO[1,5-D][1,4] BENZODIAZEPINE DERIVATIVES

(75) Inventors: Henner Knust, Rheinfeiden (DE); Heinz Stadler, Rheinfelden (CH); Andrew William Thomas, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 321 days.

(21) Appl. No.: 12/618,802

(22) Filed: Nov. 16, 2009

(65) Prior Publication Data

US 2010/0075954 A1 Mar. 25, 2010

Related U.S. Application Data

(63) Continuation of application No. 11/245,736, filed on Oct. 7, 2005, now Pat. No. 7,671,048.

(30) Foreign Application Priority Data

Oct. 12, 2004 (EP) .................................... 04105000

(51) Int. Cl.
A61P 25/00 (2006.01)
A61K 31/55 (2006.01)
C07D 487/14 (2006.01)
(52) U.S. Cl. ........................ 514/219; 540/555
(58) Field of Classification Search ............... 514/219; 540/555
See application file for complete search history.

(56) References Cited

U.S. PATENT DOCUMENTS

| 4,316,839 | A | 2/1982 | Gerecke et al. |
| 4,772,599 | A | 9/1988 | Wätjen |
| 4,775,671 | A | 10/1988 | Hunkeler et al. |
| 4,897,392 | A | 1/1990 | Tegeler et al. |
| 5,387,585 | A | 2/1995 | Borer et al. |

FOREIGN PATENT DOCUMENTS

| EP | 0027214 | 4/1981 |
| EP | 0150040 | 1/1985 |
| EP | 0519307 | 10/1992 |
| WO | 0240487 | 5/2002 |

OTHER PUBLICATIONS

McNamara, et al., Psychobiology (1993), vol. 21(2) pp. 101-108.
Gerecke et al., Heterocycles (1994), vol. 39, No. 2, pp. 693-721.
Breuer, Tetrahedron Letters (1976) No. 23, pp. 1935-1938.
Möhler et al., Nature (1981) vol. 294 pp. 763-765.
Möhler et al., Journal of Neurochemistry (1981), vol. 37(3), pp. 714-722.
Chemical Abstract 204054p, vol. 90, 1979 p. 624.
Chemical Abstract 37799s, vol. 108, 1988 p. 635.
Drug Evaluations, 6th Ed. (1986), American Medical Association, pp. 160-162.
Thompson et al., The New England Journal of Medicine (1990), vol. 323(7) pp. 445-448.
Rennie, Scientific American (1992) pp. 20 & 26.
Berkow et al., The Merck Manual of Diagnosis & Therapy, 15th Ed. (1987) pp. 839-840.
Wyngaarden, et al., Cecil Textbook of Medicine, 19th Ed. (1992), pp. 2075-2079.
Thomas, Bioorganic & Medicinal Letters, vol. 12, pp. 1881-1884 (2002).
Japanese Office Action dated Nov. 24, 2010 in Corresponding App. 2007-536039.
(Translated Japanese Office Act for Corres Jap Appl 2007536039 Nov. 8, 2011).
Richards, J.G. et al., Brain Research Bulletin 45(4):381-387 (1998).

*Primary Examiner* — Brenda Coleman
(74) *Attorney, Agent, or Firm* — George W. Johnston; Patricia S. Rocha-Tramaloni; Kimberly J. Prior

(57) ABSTRACT

The present invention is concerned with a method of treating Alzheimer's disease by administering a therapeutically effective amount of a substituted imidazo[1,5-a][1,2,4]triazolo[1,5-d][1,4]benzodiazepine of formula I

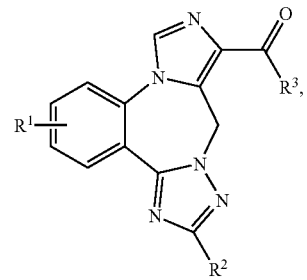

wherein $R^1$, $R^2$, and $R^3$ are as defined herein, and their pharmaceutically acceptable acid addition salts. The invention also provides novel compounds of formula I-A and pharmaceutical compositions containing them.

10 Claims, No Drawings

SUBSTITUTED IMIDAZO[1,5-A][1,2,4]TRIAZOLO[1,5-D][1,4] BENZODIAZEPINE DERIVATIVES

PRIORITY TO RELATED APPLICATIONS

This application is a continuation of U.S. application Ser. No. 11/245,736, filed Oct. 7, 2005, now pending; which claims the benefit of European Application No. 04105000.6, filed Oct. 12, 2004. The entire contents of the above-identified applications are hereby incorporated by reference.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in *Psychobiology*, 21:101-108 that the benzodiazepine receptor inverse agonist β-CCM enhance spatial learning in the Morris water-maze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides a method for the treatment of anxiety or cognitive diseases, such as Alzheimer's disease and schizophrenia, which comprises administering substituted imidazo[1,5-a][1,2,4]triazolo[1,5-d][1,4]benzodiazepine derivatives of the following formula

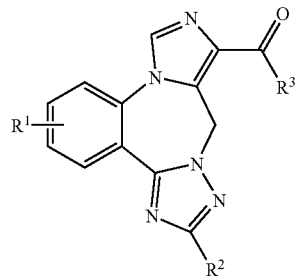

wherein
$R^1$ is halogen, lower alkyl, lower alkynyl, cycloalkyl, lower alkoxy, $OCF_3$, —NHR, —NHC(O)R or —$NHSO_2R$;
$R^2$ is hydrogen, methyl or aryl which is unsubstituted or substituted by one or two substituents selected from the group consisting of halogen and lower alkoxy;
$R^3$ is hydrogen, lower alkyl, lower alkenyl, cycloalkyl, lower alkoxy, —$O(CH_2)_{n+1}$-O-lower alkyl, —$(CH_2)_n$-aryl which is optionally substituted by lower alkyl or halogen, heteroaryl, —NHR, —$N(R)_2$, wherein each R can be the same or different, —$NHCH_2C{=}CH$, or pyrrolidin-1-one;
R is hydrogen, lower alkyl, lower alkyl substituted by halogen, heteroaryl, —$(CH_2)_n$O-lower alkyl, —NH-lower alkyl, cycloalkyl or aryl, and
n is 0, 1, 2 or 3;
and pharmaceutically acceptable acid addition salts thereof.

Compounds of formula I, wherein $R^3$ is lower alkoxy or hydrogen, have been described in EP 0 519 307 as intermediates for the preparation of tetracyclic imidazodiazepines having an aromatic heterocyclic substitution in the $R^3$ position for the treatment of diseases, related to the benzodiazepine receptor, such as epilepsy, anxiety, sleep disorders, symptoms of schizophrenia or senile dementia.

Now it has been found that this class of compounds of formula I show high affinity and selectivity for GABA A α5 receptor binding sites and might be useful as a cognitive enhancer or for the treatment of cognitive disorders like Alzheimer's disease.

The present invention further provides novel compounds of formula I-A:

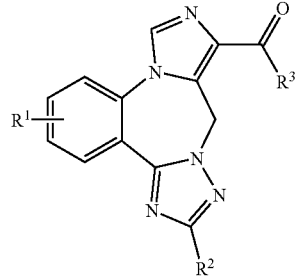

wherein
$R^1$ is halogen, lower alkyl, lower alkynyl, cycloalkyl, lower alkoxy, $OCF_3$, —NHR, —NHC(O)R or —$NHSO_2R$;
$R^2$ is hydrogen, methyl or aryl which is unsubstituted or substituted by one or two substituents selected from the group consisting of halogen and lower alkoxy;
$R^3$ is lower alkyl, lower alkenyl, cycloalkyl, —$O(CH_2)_{n+1}$—O-lower alkyl, —$(CH_2)_n$-aryl which is optionally substituted by lower alkyl or halogen, heteroaryl, —NHR, —N(R)$_2$, wherein R can be the same or different, —NHCH$_2$C≡CH, or pyrrolidin-1-one;

R is hydrogen, lower alkyl, lower alkyl substituted by halogen, heteroaryl, —(CH$_2$)$_n$O-lower alkyl, —NH-lower alkyl, cycloalkyl or aryl, and n is 0, 1, 2 or 3;

and their pharmaceutically acceptable acid addition salts thereof.

Examples of such compounds include, but are not limited to,

1-[3-fluoro-9H-imidazo[1,5-a][1,2,4]triazolo[1,5-d][1,4] benzodiazepin-10-yl]-ethanone, 1-[3-fluoro-9H-imidazo[1,5-a][1,2,4]triazolo[1,5-d][1,4] benzodiazepin-10-yl]-propan-1-one, cyclopropyl-[3-fluoro-9H-imidazo[1,5-a][1,2,4]triazolo[1,5-d][1,4]benzodiazepin-10-yl]-methanone, 1-[3-fluoro-9H-imidazo[1,5-a][1,2,4]triazolo[1,5-d][1,4] benzodiazepin-10-yl]-4-phenyl-butan-1-one, 1-[3-chloro-9H-imidazo[1,5-a][1,2,4]triazolo[1,5-d][1,4] benzodiazepin-10-yl]-propan-1-one, cyclopropyl-[3-chloro-9H-imidazo[1,5-a][1,2,4]triazolo[1,5-d][1,4]benzodiazepin-10-yl]-methanone, 1-[3-bromo-9H-imidazo[1,5-a][1,2,4]triazolo[1,5-d][1,4] benzodiazepin-10-yl]-propan-1-one, cyclopropyl-[3-bromo-9H-imidazo[1,5-a][1,2,4]triazolo[1,5-d][1,4]benzodiazepin-10-yl]-methanone, 1-[[3-fluoro-9H-imidazo[1,5-a][1,2,4]triazolo[1,5-d][1,4] benzodiazepin-10-yl]carbonyl]-2-pyrrolidinone, 3-fluoro-9H-imidazo[1,5-a][1,2,4]triazolo[1,5-d][1,4]benzodiazepine-10-carboxylic acid prop-2-ynylamide, 3-fluoro-9H-imidazo[1,5-a][1,2,4]triazolo[1,5-d][1,4]benzodiazepine-10-carboxylic acid benzylamide, 2-methoxy-ethyl 3-bromo-9H-imidazo[1,5-a][1,2,4]triazolo[1,5-d][1,4]benzodiazepine-10-carboxylate, 1-[3-bromo-9H-imidazo[1,5-a][1,2,4]triazolo[1,5-d][1,4] benzodiazepin-10-yl]-butan-1-one, 1-[3-bromo-9H-imidazo[1,5-a][1,2,4]triazolo[1,5-d][1,4] benzodiazepin-10-yl]-pentan-1-one, 1-[3-bromo-9H-imidazo[1,5-a][1,2,4]triazolo[1,5-d][1,4] benzodiazepin-10-yl]-but-2(E)-en-1-one,

[3-bromo-9H-imidazo[1,5-a][1,2,4]triazolo[1,5-d][1,4]benzodiazepin-10-yl]-o-tolyl-methanone, 1-[3-bromo-9H-imidazo[1,5-a][1,2,4]triazolo[1,5-d][1,4] benzodiazepin-10-yl]-ethanone, 1-[3-bromo-9H-imidazo[1,5-a][1,2,4]triazolo[1,5-d][1,4] benzodiazepin-10-yl]-3-methyl-butan-1-one, 1-[3-bromo-9H-imidazo[1,5-a][1,2,4]triazolo[1,5-d][1,4] benzodiazepin-10-yl]-2-phenyl-ethanone, 1-[3-bromo-9H-imidazo[1,5-a][1,2,4]triazolo[1,5-d][1,4] benzodiazepin-10-yl]-3-phenyl-propan-1-one,

[3-bromo-9H-imidazo[1,5-a][1,2,4]triazolo[1,5-d][1,4]benzodiazepin-10-yl]-phenyl-methanone,

[3-bromo-9H-imidazo[1,5-a][1,2,4]triazolo[1,5-d][1,4]benzodiazepin-10-yl]-thiophen-2-yl-methanone, 1-[3-bromo-9H-imidazo[1,5-a][1,2,4]triazolo[1,5-d][1,4] benzodiazepin-10-yl]-2-(3-chloro-phenyl)-ethanone and 3-fluoro-9H-imidazo[1,5-a][1,2,4]triazolo[1,5-d][1,4]benzodiazepine-10-carboxylic acid cyclopropyl-amide.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain saturated hydrocarbon group containing from 1-7, preferably from 1-4, carbon atoms, for example, methyl, ethyl, propyl, isopropyl, n-butyl, i-butyl or t-butyl.

As used herein, the term "lower alkoxy" denotes a straight- or branched-chain alkyl residue containing from 1-7, preferably from 1-4, carbon atoms that is attached via an oxygen atom. Examples of "lower alkoxy" residues include methoxy, ethoxy, isopropoxy and the like.

As used herein, the term "lower alkenyl" denotes a straight- or branched-chain unsaturated hydrocarbon containing from 2-7, preferably from 2-4, carbon atoms with at least one double bond. Examples of "lower alkenyl" residues include ethenyl, propenyl and the like.

As used herein, the term "lower alkynyl" denotes a straight- or branched-chain unsaturated hydrocarbon containing from 2-7, preferably from 2-4, carbon atoms with at least one triple bond. Examples of "lower alkynyl" residues include ethynyl, propynyl and the like.

As used herein, the term "lower alkyl substituted by halogen" denotes a straight- or branched-chain alkyl group as defined above wherein at least one hydrogen atom is replaced by halogen, for example $CF_3$, $CH_2F$, $CHF_2$, $CH_2CF_3$.

The term "halogen" denotes chlorine, iodine, fluorine and bromine.

The term "cycloalkyl" denotes a cyclic alkyl ring, having from 3 to 7 carbon ring atoms, for example, cyclopropyl, cyclopentyl or cyclohexyl.

The term "aryl" denotes phenyl or naphthyl.

The term "heteroaryl" denotes a five or six membered aromatic ring, containing at least one heteroatom selected from O, N or S, for example thiophene, imidazole, pyrazole or pyridine.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

The term "therapeutically effective amount" means an amount that is effective to prevent, alleviate or ameliorate symptoms of disease or prolong the survival of the subject being treated.

Most preferred are compounds, which have a binding activity (Ki) of lower 15 nM and are selective for GABA A α5 subunits and are relatively free of activity at GABA A α1, α2 and α3 receptor binding sites.

Preferred compounds of formula I are those, in which $R^3$ is lower alkyl, for example the following compounds:

1-[3-fluoro-9H-imidazo[1,5-a][1,2,4]triazolo[1,5-d][1,4] benzodiazepin-10-yl]-ethanone, 1-[3-fluoro-9H-imidazo[1,5-a][1,2,4]triazolo[1,5-d][1,4] benzodiazepin-10-yl]-propan-1-one, 1-[3-chloro-9H-imidazo[1,5-a][1,2,4]triazolo[1,5-d][1,4] benzodiazepin-10-yl]-propan-1-one, 1-[3-bromo-9H-imidazo[1,5-a][1,2,4]triazolo[1,5-d][1,4] benzodiazepin-10-yl]-propan-1-one, 1-[3-bromo-9H-imidazo[1,5-a][1,2,4]triazolo[1,5-d][1,4] benzodiazepin-10-yl]-butan-1-one and 1-[3-bromo-9H-imidazo[1,5-a][1,2,4]triazolo[1,5-d][1,4] benzodiazepin-10-yl]-3-methyl-butan-1-one.

Further preferred are compounds, wherein $R^3$ is cycloalkyl, for example the following compounds:

cyclopropyl-[3-fluoro-9H-imidazo[1,5-a][1,2,4]triazolo[1,5-d][1,4]benzodiazepin-10-yl]-methanone, cyclopropyl-[3-chloro-9H-imidazo[1,5-a][1,2,4]triazolo[1,5-d][1,4]benzodiazepin-10-yl]-methanone and cyclopropyl-[3-bromo-9H-imidazo[1,5-a][1,2,4]triazolo[1,5-d][1,4]benzodiazepin-10-yl]-methanone.

Preferred compounds of formula I are further those, in which $R^3$ is —$(CH_2)_n$-phenyl, for example the compounds 1-[3-fluoro-9H-imidazo[1,5-a][1,2,4]triazolo[1,5-d][1,4]benzodiazepin-10-yl]-4-phenyl-butan-1-one and 1-[3-bromo-9H-imidazo[1,5-a][1,2,4]triazolo[1,5-d][1,4]benzodiazepin-10-yl]-3-phenyl-propan-1-one.

Preferred compounds of formula I are further those, in which $R^3$ is alkoxy, for example the compounds ethyl 3-cyclopropyl-9H-imidazo[1,5-a][1,2,4]triazolo[1,5-d][1,4]benzodiazepine-10-carboxylate, ethyl 3-methoxy-9H-imidazo[1,5-a][1,2,4]triazolo[1,5-d][1,4]benzodiazepine-10-carboxylate, ethyl 3-acetylamino-9H-imidazo[1,5-a][1,2,4]triazolo[1,5-d][1,4]benzodiazepine-10-carboxylate, ethyl 3-trifluoromethoxy-9H-imidazo[1,5-a][1,2,4]triazolo[1,5-d][1,4]benzodiazepine-10-carboxylate, ethyl 3-bromo-9H-imidazo[1,5-a][1,2,4]triazolo[1,5-d][1,4]benzodiazepine-10-carboxylate, ethyl 3-ethynyl-9H-imidazo[1,5-a][1,2,4]triazolo[1,5-d][1,4]benzodiazepine-10-carboxylate, ethyl 3-(2,2,2-trifluoro-acetylamino)-9H-imidazo[1,5-a][1,2,4]triazolo[1,5-d][1,4]benzodiazepine-10-carboxylate, ethyl 3-isobutyrylamino-9H-imidazo[1,5-a][1,2,4]triazolo[1,5-d][1,4]benzodiazepine-10-carboxylate, ethyl 3-(3-methoxy-propionylamino)-9H-imidazo[1,5-a][1,2,4]triazolo[1,5-d][1,4]benzodiazepine-10-carboxylate, ethyl 3-formylamino-9H-imidazo[1,5-a][1,2,4]triazolo[1,5-d][1,4]benzodiazepine-10-carboxylate, ethyl 3-ethoxycarbonylamino-9H-imidazo[1,5-a][1,2,4]triazolo[1,5-d][1,4]benzodiazepine-10-carboxylate and ethyl 3-(3-ethyl-ureido)-9H-imidazo[1,5-a][1,2,4]triazolo[1,5-d][1,4]benzodiazepine-10-carboxylate.

Preferred compounds of formula I are further those, in which $R^3$ is hydrogen, for example the compounds 3-bromo-9H-imidazo[1,5-a][1,2,4]triazolo[1,5-d][1,4]benzodiazepine-10-carbaldehyde and 3-chloro-9H-imidazo[1,5-a][1,2,4]triazolo[1,5-d][1,4]benzodiazepine-10-carbaldehyde.

Preferred compounds of formula I are further those, in which $R^3$ is —$NHCH_2C \equiv CH$, for example the compound 3-fluoro-9H-imidazo[1,5-a][1,2,4]triazolo[1,5-d][1,4]benzodiazepine-10-carboxylic acid prop-2-ynylamide.

The present compounds of formula I and their pharmaceutically acceptable salts can be prepared by methods known in the art, for example, by processes described below, which processes comprise a) reacting a compound of formula II

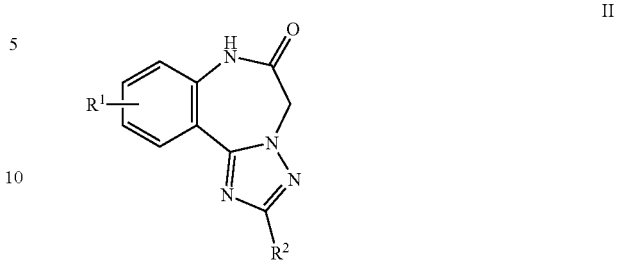

with an activating agent, such as phosphorous oxide chloride (for X=Cl), or with diphenylphosphorylchloride (for X=—OP(O)(OPh)$_2$) to produce a compound of formula III

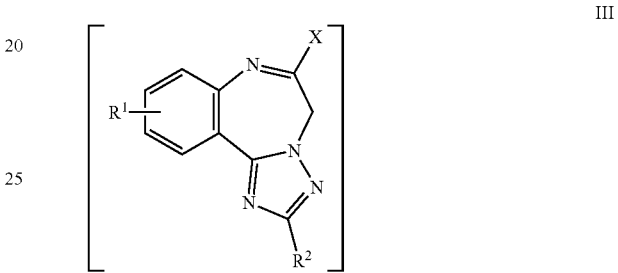

which may be isolated or may be directly reacted with a mixture of lithium diisopropylamide or lithium hexamethyldisilazide and (E)-(dimethylamino-methylamino)-acetic acid ethyl ester or ethylisocyanoacetate to produce a compound of formula I-1

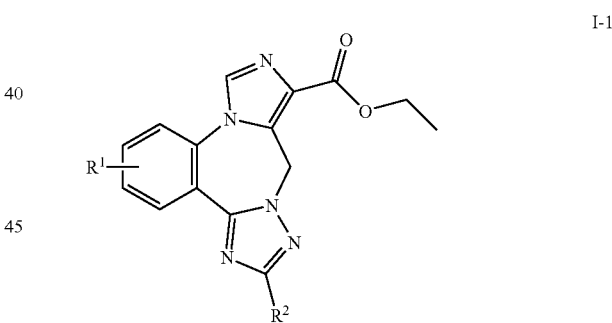

wherein $R^1$ and $R^2$ have the meaning as described above, or b) reacting a compound of formula IV

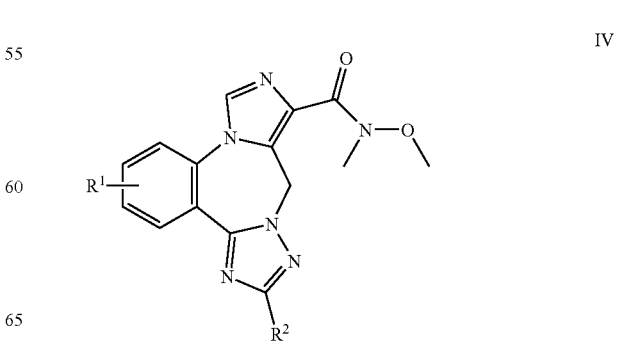

with a compound of formula

R³MgX to produce a compound of formula I-2

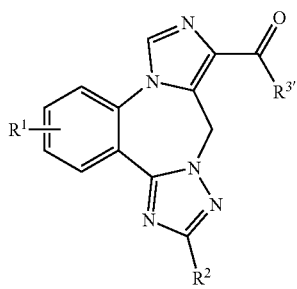

I-2 wherein R³' is lower alkyl, cycloalkyl, —(CH₂)-aryl optionally substituted by lower alkyl or halogen, heteroaryl, and R¹ and R² are as described above, or c) reacting a compound of formula V

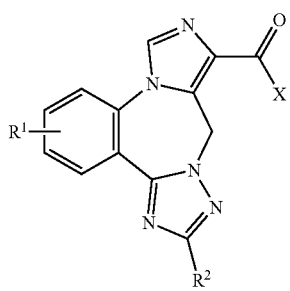

V with a compound of formulas

NH₂R, NH(R)₂, wherein each R can be the same or different, NH₂CH₂C≡CH, or pyrrolidin-1-one to a compound of formula I-3

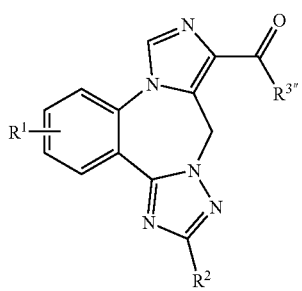

I-3 wherein R³" is —NHR, —N(R)₂, wherein each R can be the same or different, or is —NHCH₂C≡CH, or pyrrolidin-1-one; and R¹ and R² are as described above, or d) reacting a compound of formula VI

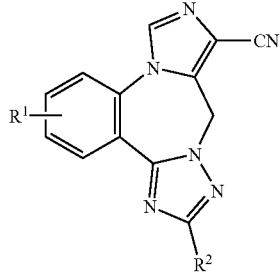

VI with a compound of formula

R³MgX to produce a compound of formula I-2

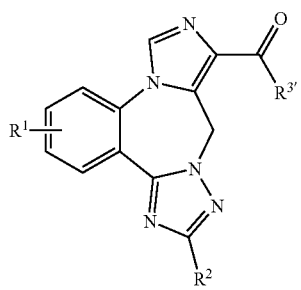

I-2 wherein R³' is lower alkyl, cycloalkyl, —(CH₂)-aryl optionally substituted by lower alkyl or halogen, heteroaryl, and R¹ and R² are as described above, or e) reacting a compound of formula VII

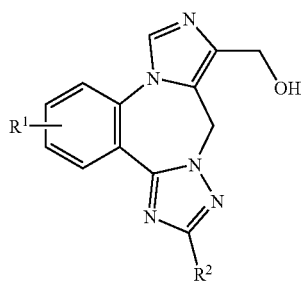

VII with manganese(IV) oxide
to produce an aldehyde of formula I-4

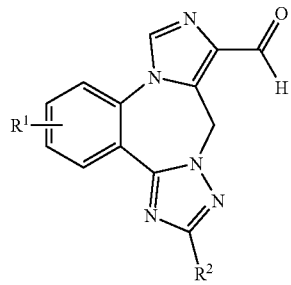

I-4 wherein $R^1$ and $R^2$ are as described above,
and, if desired, converting a compound of formula I into a pharmaceutically acceptable salt.

The following schemes (scheme 1-8) describe the processes for preparation of compounds of formula I in more detail. The starting materials are known compounds or may be prepared according to methods known in the art.

Scheme 1

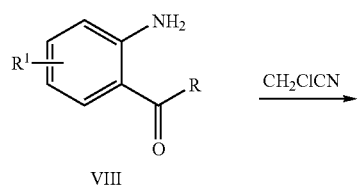

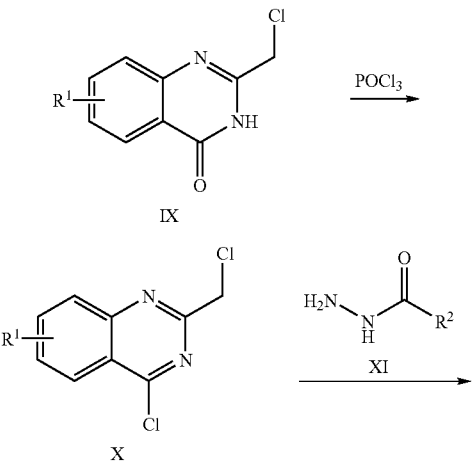

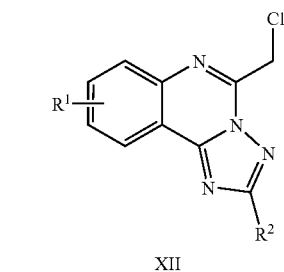

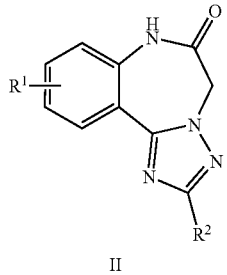

II

In accordance with Scheme 1, a corresponding intermediate compound of formula II is known and can be prepared by methods, known in the art, for example in the following way.

A corresponding compound of formula VIII, a $R^1$-substituted 2-aminobenzoic acid derivative, and chloroacetonitrile are dissolved in dioxane, and a weak stream of dry HCl is introduced at 5° C. to 15° C. for a period of several hours. After addition of further chloroacetonitrile, the mixture is stirred at ambient temperature for several hours. The obtained compound of formula IX is purified in a conventional manner and dissolved in chloroform in the presence of N,N-dimethyl-p-toluidine. Phosphorous oxide chloride is added and the solution heated. The obtained compound of formula X is purified by known methods and heated with a compound of formula XI, an acylhydrazide, in toluene for several hours affording a compound of formula XII, for example the compound 5-chloromethyl-9-fluoro-1,2,4-triazolo[4,3-c]quinazoline. Finally, a compound of formula II is obtained by dissolving a compound of formula XII in dioxane and treatment with aqueous sodium hydroxide in such a manner that the reaction temperature is between 10° C. to 15° C. Conventional workup and purification affords a corresponding intermediate of formula II, for example 10-fluoro-5H-[1,2,4]triazolo[1,5-d][1,4]benzodiazepin-6(7H)-one.

Scheme 2

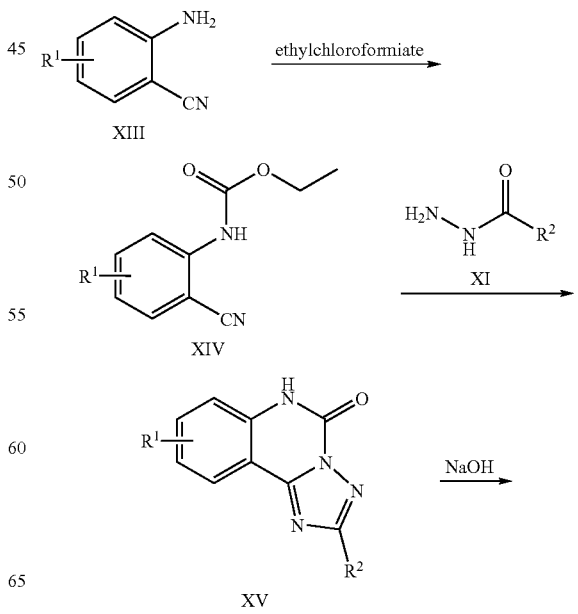

Scheme 3

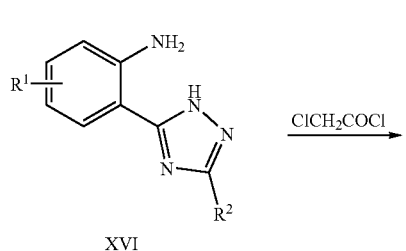

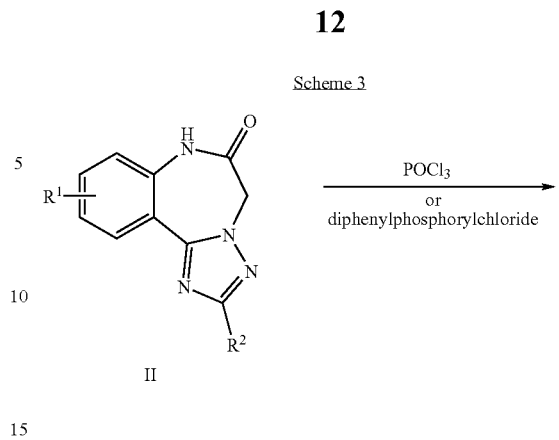

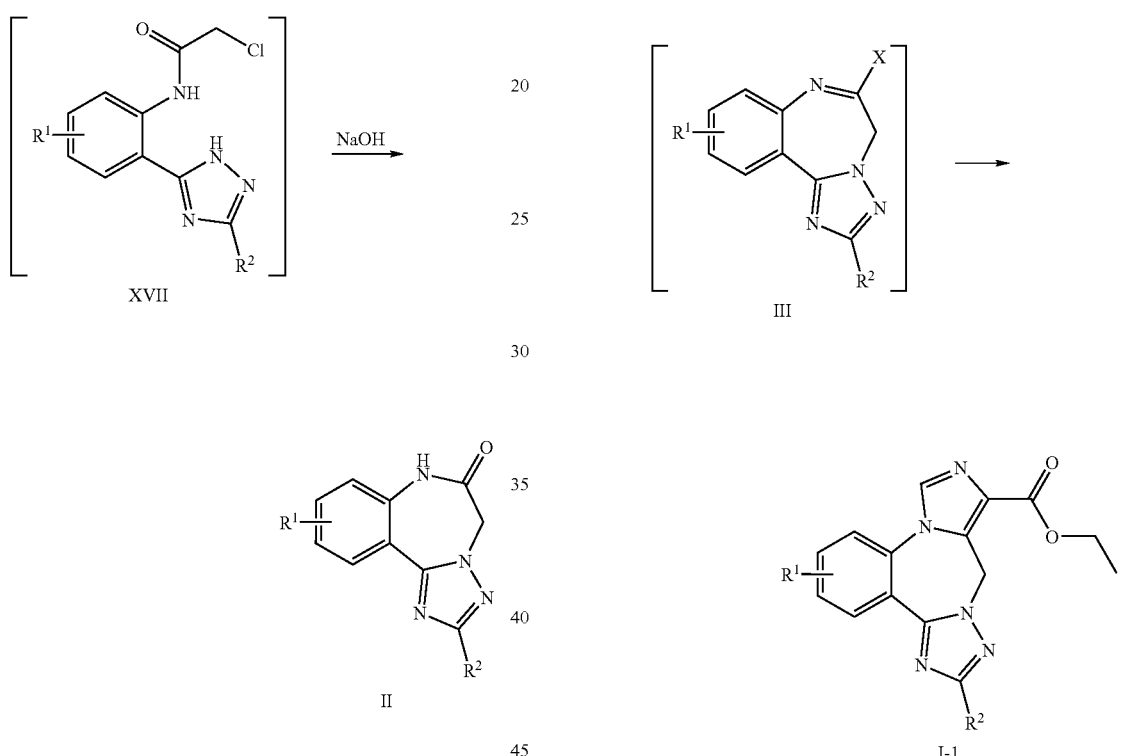

In accordance with Scheme 2, a corresponding intermediate compound of formula II may be prepared alternatively in the following way:

A corresponding compound of formula XIII, an R'-substituted 2-aminobenzonitrile, is heated with ethyl chloroformate to obtain a carbamic acid ester of formula XIV, which is treated with a compound of formula XI, an azylhydrazide, in 1-methyl-2-pyrrolidone at 160° C. under removal of ethanol. Conventional workup provides a urea of formula XV which is heated with aqueous sodium hydroxide in ethylenglycol to obtain a compound of formula XVI. Treatment of a compound of formula XVI with chloroacetyl chloride in acetic acid provides an amide of formula XVII, which is treated with aqueous sodium hydroxide in dioxane at ambient temperature to obtain the intermediate of formula II. Alternatively, a compound of formula XVI can be directly transformed to a compound of formula II by dissolving a compound of formula XVI in dioxane and pyridine and adding dropwise chloroacetyl chloride at a temperature between 10° C. to 15° C. After stirring for a short period of time aqueous sodium hydroxide is added and the reaction mixture stirred for several hours at ambient temperature to obtain the compound of formula II.

X = halogen (Cl) or —OP(O)(OPh)$_2$

In accordance with Scheme 3, a compound of formula II is treated with an activation agent in the presence of base at elevated temperature, for example, phosphorous oxide chloride in toluene or chloroform in the presence of N,N-dimethyl-p-toluidine, to obtain a compound of formula III which is isolated in conventional manner or directly used in the next reaction step. Finally, a compound of formula I-1 is obtained by the reaction of III with a mixture of a cooled solution of lithium diisopropylamide or lithium hexamethyldisilazide in THF and (E)-(dimethylamino-methylenamino)-acetic acid ethyl ester or with a mixture of a cooled solution of ethyl isocyanoacetate in THF and potassium tert-butoxide or sodium hydride.

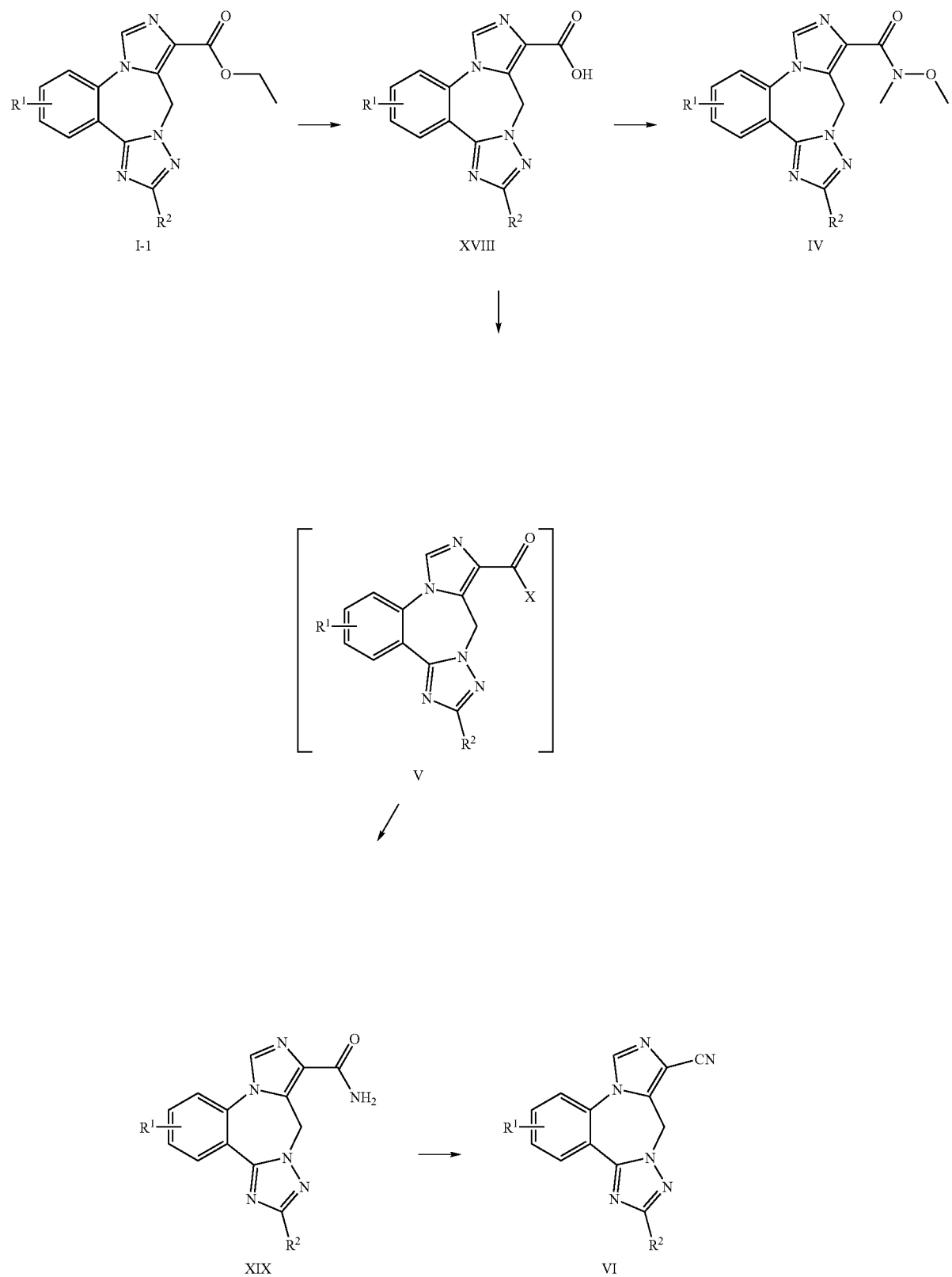
Scheme 4 wherein X is halogen and the other definitions are as described above.

According to Scheme 4, a carboxylic ester of formula I-1, is saponified to a corresponding carboxylic acid of formula II, which can be treated with an activation reagent, for example 1-(3-dimethylaminopropyl)-3-ethylcarbodiimide hydrochloride, in the presence of N,O-dimethylhydroxylamine hydrochloride and a base, for example N-methylmorpholine, in a solvent mixture of dichloromethane and DMF at ambient temperature to afford a compound of formula III.

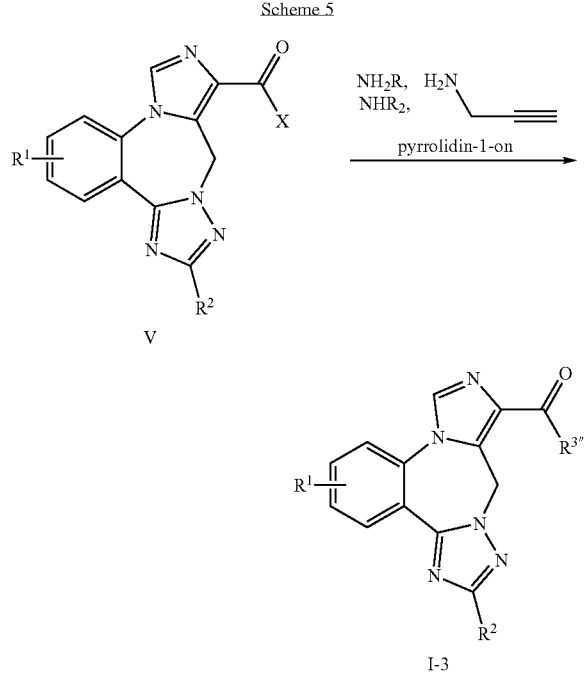

Scheme 5

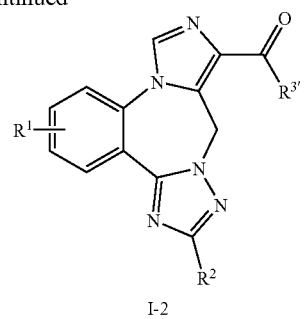

I-2 wherein $R^1$ and $R^2$ are as described above and $R^{3'}$ is lower alkyl, cycloalkyl, —(CH$_2$)-aryl, optionally substituted by lower alkyl or halogen, heteroaryl, and $R^1$ and $R^2$ are as described above.

An amide of formula IV can be transformed in a corresponding ketone of general formula I-2 by reaction with an appropriate Grignard reagent, for example methylmagnesium chloride, in a suitable solvent, for example THF or the like, at ambient or elevated temperature. An alternative synthetic route to these ketones of formula I-2 would involve the activation of a carboxylic acid of formula XVIII followed by treatment with ammoniumhydroxide to obtain the carboxylic amide of formula XIX. Reaction of XIX with suitable reagents, for example pyridine and trifluoroacetic anhydride, in an appropriate solvent, for example dioxane or the like, leads to the corresponding cyano-compounds of formula VI, and in accordance with scheme 7, compounds of formula VI can be treated with an appropriate Grignard reagent, for example methylmagnesium chloride, in a suitable solvent, for example THF or the like, at ambient or elevated temperature affording ketones of the general formula I-2.

wherein X is halogen and $R^{3'''}$ is —NHR, —N(R)$_2$, wherein each R can be the same or different, —NHCH$_2$C≡CH or pyrrolidin-1-one, and R and $R^1$ and $R^2$ are as described above.

Amides of the general formula I-3 can be obtained by activation of a carboxylic acid of formula II followed by reaction with an amine, for example benzylamine, in a suitable solvent, for example DMF or the like at ambient or elevated temperature.

Scheme 7

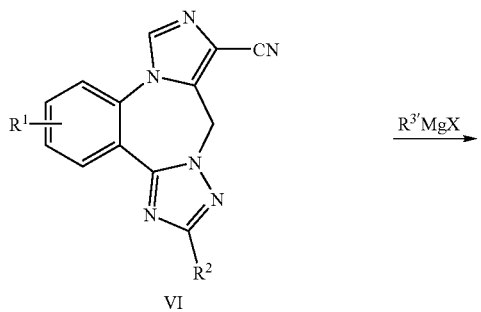

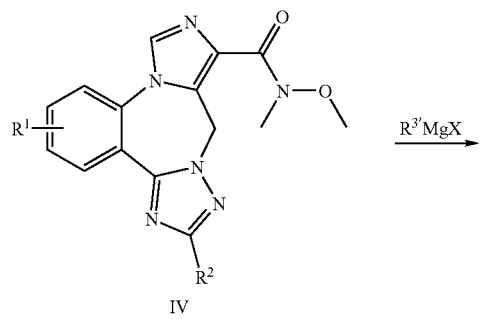

Scheme 6

I-2 wherein $R^1$ and $R^2$ are as described above and $R^{3'}$ is lower alkyl, cycloalkyl, —(CH$_2$)$_n$-aryl optionally substituted by lower alkyl or halogen, or heteroaryl,

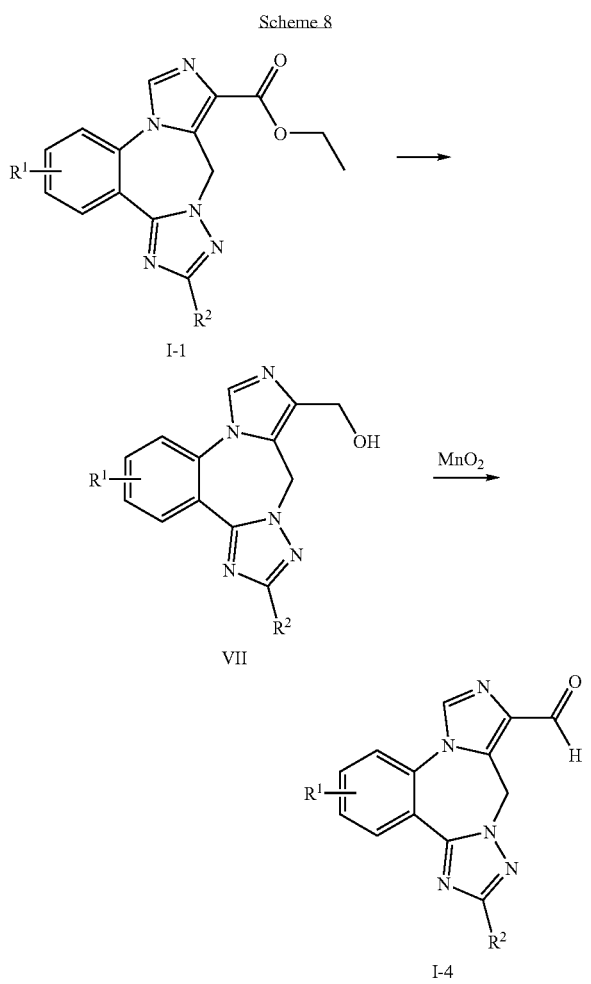

Scheme 8

According to scheme 8, a compound of formula I-1 is heated with a reducing agent, for example lithiumborohydride or the like, in a suitable solvent, for example tetrahydrofuran or the like, to obtain an alcohol of formula VII which is oxidized by treatment with manganese(IV) oxide in dichloromethane at ambient temperature to obtain an aldehyde of general formula I-4.

As mentioned earlier, the compounds of formula I and their pharmaceutically acceptable acid addition salts possess valuable pharmacological properties. It has been found that the compounds of the present invention are ligands for GABA A receptors containing the α5 subunit and are therefore useful in the therapy where cognition enhancement is required.

The compounds were investigated in accordance with the test given hereinafter.

Membrane Preparation and Binding Assay

The affinity of compounds at GABA A receptor subtypes was measured by competition for [$^3$H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM $CaCl_2$, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 μL (96-well plates) which contained 100 μL of cell membranes, [$^3$H]flumazenil at a concentration of 1 nM for α1, α2, α3 subunits and 0.5 nM for α5 subunits and the test compound in the range of $10^{-10}$–$3\times10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and all were found to possess a Ki value for displacement of [$^3$H]flumazenil from α5 subunits of the rat GABA A receptor of 100 nM or less. In a preferred embodiment the compounds of the invention are binding selective for the α5 subunit relative to the α1, α2 and α3 subunit.

In the table below it is shown the activity data of some preferred compounds:

| Example No. | Ki[nM] hα1 | Ki[nM] hα2 | Ki[nM] hα3 | Ki[nM] hα5 |
|---|---|---|---|---|
| 1 | 313.9 | 183.1 | 232.7 | 104.1 |
| 2 | 6.2 | 3.4 | 3.9 | 2.2 |
| 3 | 2.8 | 2.0 | 1.8 | 1.2 |
| 4 | 45.6 | 60.0 | 55.9 | 16.4 |
| 5 | 32.2 | 28.1 | 22.4 | 2.7 |
| 6 | 14.5 | 18.0 | 19.9 | 2.2 |
| 9 | 12.3 | 12.3 | 9.0 | 5.8 |
| 10 | 242.1 | 67.8 | 64.9 | 67.8 |
| 12 | 1.7 | 0.9 | 0.7 | 0.6 |
| 14 | 0.9 | 1.7 | 0.9 | 0.2 |
| 19 | 3.4 | 1.1 | 1.4 | 0.7 |
| 21 | 223.4 | 134.1 | 71.9 | 5.9 |
| 23 | 1.9 | 3.8 | 1.8 | 0.3 |
| 24 | 10.6 | 4.4 | 6.4 | 0.6 |
| 25 | 20.3 | 28.5 | 18.8 | 1.4 |
| 26 | 85.1 | 106.4 | 72.7 | 3.5 |
| 31 | 243.2 | 260.8 | 172.6 | 8.3 |
| 33 | 108.6 | 159.8 | 132.7 | 3.8 |
| 38 | 3.1 | 7.3 | 5.7 | 1.2 |
| 39 | 11.4 | 73.5 | 39.7 | 6.4 |
| 41 | 9.7 | 24.8 | 17.7 | 5.1 |
| 42 | 6.5 | 8.6 | 4.9 | 2.0 |
| 43 | 5.3 | 22.0 | 14.4 | 2.6 |
| 44 | 20.3 | 26.0 | 12.4 | 6.9 |

The present invention also provides pharmaceutical compositions containing compounds of the invention or pharmaceutically acceptable acid addition salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of the invention and, if desired, one or more other therapeutically valuable substances into a galenical administration form together with one or more therapeutically inert carrier.

The compounds and compositions of the invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical composition also can be administered rectally, for example, in the form of suppositories, or parenterally, for example, in the form of injectable solutions. Compounds of the invention are selective high affinity and selectivity for GABA A α5 receptor binding sites. The present invention also provides methods of treating CNS diseases. Such methods include a method for treating a disease selected from the group consisting of cognitive disorders, anxiety, Alzheimer's disease, and schizophrenia which comprises administering to an individual a therapeutically effective amount of a compound of the invention, for example, a compound of formula I, or a pharmaceutically acceptable salt thereof. In one embodiment, the invention provides a method of treating Alzheimer's disease by administering to an individual a therapeutically effective amount of a compound of formula I or a pharmaceutically acceptable salt thereof.

The dosage at which the compound of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

| | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

| | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

| | mg/supp. |
|---|---|
| Active substance | 15 |
| Suppository mass | 1285 |
| Total | 1300 |

The suppository mass is melted in a glass or steel vessel, mixed thoroughly and cooled to 45° C.

Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples are provided for illustration of the invention. They should not be considered as limiting the scope of the invention, but merely as being representative thereof.

EXAMPLE 1

1-[3-Fluoro-9H-imidazo[1,5-a][1,2,4]triazolo[1,5-d][1,4]benzodiazepin-10-yl]-ethanone To a solution of 10-cyano-3-fluoro-9H-imidazo[1,5-a][1,2,4]triazolo[1,5-d][1,4]benzodiazepine[1] (2.07 g, 7.78 mmol) in THF (100 mL) was added at ambient temperature methylmagnesium bromide (3 N in Et$_2$O, 39.0 mL, 13.0 mmol) over a period of 5 min. The resulting clear brown solution was stirred for another 2 h. The mixture was carefully poured into aq. HCl (1 N, 200 mL) and extracted with ethyl acetate (3×200 mL). The combined organic layers were washed with water (250 mL) and brine (250 mL), dried over sodium sulfate and concentrated. Purification of the residue by chromatography (SiO$_2$, heptane:ethyl acetate:methanol=20:80:0 to 0:90:10) afforded the title compound (303 mg, 14%) as a white solid. MS: m/e=282.4 (M−H$^-$).

EXAMPLE 2

1-[3-Fluoro-9H-imidazo[1,5-a][1,2,4]triazolo[1,5-d] [1,4]benzodiazepin-10-yl]-propan-1-one a) 3-Fluoro-9H-imidazo[1,5-a][1,2,4]triazolo[1,5-d] [1,4]-benzodiazepine-10-carboxylic acid methoxy-methyl-amide A mixture of 3-fluoro-9H-imidazo[1,5-a][1,2,4]triazolo[1, 5-d][1,4]benzodiazepine-10-carboxylic acid (20.74 g, 72.7 mmol), N,O-dimethylhydroxylamine hydrochloride (11.35 g, 116.3 mmol), 1-(3-dimethylaminopropyl)-3-ethylcarbodiimide hydrochloride (16.72 g, 87.24 mmol), N-methylmorpholine (12.78 mL, 116.3 mmol) and N,N-dimethylaminopyridine (300 mg, 3.23 mmol) in a mixture of THF (200 mL) and DMF (40 mL) was stirred at ambient temperature for 18 h. The dichloromethane was distilled off and ice cold water (200 mL) was added. The resulting suspension was stirred for 15 min, filtered and washed with water (100 mL). Drying afforded the title compound (11.46 g, 48%) as white solid. MS: m/e=329.1 (M+H$^+$).

b) 1-[3-fluoro-9H-imidazo[1,5-a][1,2,4]triazolo[1,5-d][1,4]-benzodiazepin-10-yl]-propan-1-one To a solution of 3-fluoro-9H-imidazo[1,5-a][1,2,4]triazolo [1,5-d][1,4]benzodiazepine-10-carboxylic acid methoxy-methyl-amide (500 mg, 1.52 mmol) in THF (20 mL) was added at 7-70° C. ethyl magnesium bromide (3M in THF, 1.52 mL, 4.57 mmol). The dry ice bath was removed and the reaction mixture was stirred for 2 h. After cooling to −70° C. further ethyl magnesium bromide (3M in THF, 1.52 mL, 4.57 mmol) was added and the mixture stirred for another 2 h at ambient temperature. The mixture was cooled to 0° C. and aqueous HCl (1 N, 10 mL) was added dropwise. It was diluted with ethyl acetate (20 mL) and aqueous Na$_2$CO$_3$ (sat.). The aqueous layer was extracted with ethyl acetate and the combined organic layers were washed with aqueous Na$_2$CO$_3$ (sat.). Drying over sodium sulfate and purification of the residue by chromatography (SiO$_2$, heptane:ethyl acetate: dichloromethane=60:20:20 to 30:50:20:) afforded the title compound (200 mg, 44%) as a white solid. MS: m/e=298.2 (M+H$^+$).

EXAMPLE 3

Cyclopropyl-[3-fluoro-9H-imidazo[1,5-a][1,2,4] triazolo[1,5-d][1,4]benzodiazepin-10-yl]-methanone a) 3-Fluoro-10-hydroxymethyl-9H-imidazo[1,5-a][1, 2,4]triazolo[1,5-d][1,4]-benzodiazepine To a suspension of ethyl 3-fluoro-9H-imidazo[1,5-a][1,2, 4]triazolo[1,5-d][1,4]benzodiazepine-10-carboxylate[1] (9.24 g, 29.5 mmol) in THF (300 mL) was added lithium borohydride (811 mg, 35.4 mmol) and the reaction mixture was heated to reflux for 8 hrs. After cooling to ambient temperature, it was acidified to pH=2 by adding aqueous HCl (1 N). The solvent was evaporated and the residue was taken in aq. NH$_4$OH (conc., 100 mL). The resulting solid were filtered off, washed with water (3×10 mL) and dried (60° C., vacuo) affording the title compound (6.53 g, 83%) as a white solid. MS: m/e=272.2 (M+H$^+$).

b) 3-Fluoro-9H-imidazo[1,5-a][1,2,4]triazolo[1,5-d] [1,4]-benzodiazepine-10-carbaldehyde To a suspension of 3-fluoro-10-hydroxymethyl-9H-imidazo[1,5-a][1,2,4]triazolo[1,5-d][1,4]benzodiazepine (6.00 g, 22.1 mmol) in dichloromethane (200 mL) at 0° C. was added sodium bicarbonate (5.58 g, 66.4 mmol) and Dess-Martin periodinane (14.5 g, 33.2 mmol). After stirring at this temperature for 35 min it was allowed to warm to ambient temperature and stirred for another 1.5 h. Heptane (300 mL) and dichloromethane (100 mL) were added and the orange suspension was stirred for additional 2 h. After filtration through Hyflo® it was carefully washed with dichloromethane and evaporated. Purification of the residue by chromatography (SiO$_2$, ethyl acetate:methanol=19:1) afforded the title compound (5.12 g, 86% and dried in vacuo affording the title compound (208 mg, 35%) as an off-white solid. MS: m/e=270.3 (M+H$^+$).

c) Cyclopropyl-[3-fluoro-9H-imidazo[1,5-a][1,2,4] triazolo[1,5-d][1,4]benzodiazepin-10-yl]-methanol To a freshly prepared cyclopropylmagnesium bromide solution (0.91 M in THF, 35 mL, 31.9 mmol) was added dropwise at 35° C. a solution of 3-fluoro-9H-imidazo[1,5-a] [1,2,4]triazolo[1,5-d][1,4]benzodiazepine-10-carbaldehyde (3.00 g, 11.14 mmol) in THF (90 mL). The reaction mixture was stirred for 6 h at 40° C. and 10 h at ambient temperature. Aqueous NH$_4$Cl (10%, 2 mL) was added and stirring was continued for 15 min. The resulting suspension was concentrated and the residue suspended in a mixture of water and dichloromethane, filtered over Dicalit and the solid was washed with water and dichloromethane. The organic layer was washed with aqueous sodium chloride (sat.) and dried over sodium sulfate. Purification of the residue by chromatography (SiO$_2$, dichloromethane:methanol=9:1) afforded the title compound (1.60 g, 46%) as a white crystalline solid. MS: m/e=312.1 (M+H)$^+$.

d) Cyclopropyl-[3-fluoro-9H-imidazo[1,5-a][1,2,4] triazolo[1,5-d][1,4]-benzodiazepin-10-yl]-methanone To a solution of cyclopropyl-[3-fluoro-9H-imidazo[1,5-a] [1,2,4]triazolo[1,5-d][1,4]benzo-diazepin-10-yl]-methanol (500 mg, 1.61 mmol) in dichloromethane (100 mL) was added manganese(IV) oxide (5.00 g, 57.5 mmol) The reaction mixture was stirred for 3 h at ambient temperature before filtered over Dicalit, washed with dichloromethane and dried over magnesium sulfate. Recrystallisation of the residue from ethyl acetate afforded the title compound (200 mg, 40%) as a white crystalline solid. MS: m/e=310.2 (M+H)$^+$.

EXAMPLE 4

1-[3-Fluoro-9H-imidazo[1,5-a][1,2,4]triazolo[1,5-d] [1,4]benzodiazepin-10-yl]-4-phenyl-butan-1-one As described for example 3c) 3-fluoro-9H-imidazo[1,5-a] [1,2,4]triazolo[1,5-d][1,4]benzo-diazepine-10-carbaldehyde (1.50 g, 5.57 mmol), using freshly prepared 3-phenyl-propy-1magnesium bromide solution (0.68 M in THF, 25 mL, 17.1 mmol) instead of cyclopropylmagnesium bromide solution, was converted to 1-[3-fluoro-9H-imidazo[1,5-a][1,2,4]triazolo[1,5-d][1,4]benzodiazepin-10-yl]-4-phenyl-butan-1-ol (500 g, 23%) which was obtained as a light yellow foam and directly used in the next reaction step.

As described for example 3d) Cyclopropyl-[3-fluoro-9H-imidazo[1,5-a][1,2,4]triazolo[1,5-d][1,4]benzodiazepin-10-yl]-4-phenyl-butan-1-ol (800 mg, 2.05 mmol) instead of cyclopropyl-[3-fluoro-9H-imidazo[1,5-a][1,2,4]triazolo[1,5-d][1,4]benzo-diazepin-10-yl]-methanol was converted to the title compound (400 g, 50%) which was obtained as a white crystalline solid. MS: m/e=388.1 [M+H$^+$].

EXAMPLE 5

1-[3-Chloro-9H-imidazo[1,5-a][1,2,4]triazolo[1,5-d][1,4]benzodiazepin-10-yl]-propan-1-one a) 1-[3-Chloro-9H-imidazo[1,5-a][1,2,4]triazolo[1,5-d][1,4]benzodiazepin-10-yl]-propan-1-ol As described for example 3c) 3-Chloro-9H-imidazo[1,5-a][1,2,4]triazolo[1,5-d][1,4]benzodiazepine-10-carbaldehyde (2.00 g, 7.00 mmol) instead of 3-fluoro-9H-imidazo[1,5-a][1,2,4]triazolo[1,5-d][1,4]benzo-diazepine-10-carbaldehyd, using freshly prepared ethylmagnesium bromide solution (1.05 M in THF, 20 mL, 21.0 mmol) instead of cyclopropylmagnesium bromide solution, was converted to the title compound (1.30 g, 59%) which was obtained as a light yellow foam. MS: m/e=316.0 [M+H$^+$].

b) 1-[3-Chloro-9H-imidazo[1,5-a][1,2,4]triazolo[1,5-d][1,4]-benzodiazepin-10-yl]-propan-1-one As described for example 3d) 1-[3-chloro-9H-imidazo[1,5-a][1,2,4]triazolo[1,5-d][1,4]benzodiazepin-10-yl]-propan-1-ol (1.30 g, 4.12 mmol) instead of cyclopropyl-[3-fluoro-9H-imidazo[1,5-a][1,2,4]triazolo[1,5-d][1,4]benzo-diazepin-10-yl]-methanol was converted to the title compound (1.05 g, 81%) which was obtained as an off-white crystalline solid. MS: m/e=314.1 [M+H$^+$].

EXAMPLE 6

Cyclopropyl-[3-chloro-9H-imidazo[1,5-a][1,2,4]triazolo[1,5-d][1,4]benzodiazepin-10-yl]-methanone a) Cyclopropyl-[3-chloro-9H-imidazo[1,5-a][1,2,4]triazolo[1,5-d][1,4]benzodiazepin-10-yl]-methanol As described for example 3c) 3-chloro-9H-imidazo[1,5-a][1,2,4]triazolo[1,5-d][1,4]benzodiazepine-10-carbaldehyde (3.50 g, 12.3 mmol) instead of 3-fluoro-9H-imidazo[1,5-a][1,2,4]triazolo[1,5-d][1,4]benzo-diazepine-10-carbaldehyde was converted to the title compound (2.70 g, 67%) which was obtained as a white crystalline solid. MS: m/e=328.0 [M+H$^+$].

b) Cyclopropyl-[3-chloro-9H-imidazo[1,5-a][1,2,4]triazolo[1,5-d][1,4]benzodiazepin-10-yl]-methanone As described for example 3d) cyclopropyl-[3-chloro-9H-imidazo[1,5-a][1,2,4]triazolo[1,5-d][1,4]benzodiazepin-10-yl]-methanol (2.00 g, 6.10 mmol) instead of cyclopropyl-[3-fluoro-9H-imidazo[1,5-a][1,2,4]triazolo[1,5-d][1,4]benzo-diazepin-10-yl]-methanol was converted to the title compound (1.50 g, 76%) which was obtained as a white crystalline solid. MS: m/e=326.1 [M+H$^+$].

EXAMPLE 7

1-[3-Bromo-9H-imidazo[1,5-a][1,2,4]triazolo[1,5-d][1,4]benzodiazepin-10-yl]-propan-1-one 3-Bromo-9H-imidazo[1,5-a][1,2,4]triazolo[1,5-d][1,4]-benzodiazepine-10-carboxylic acid A mixture of ethyl 3-bromo-9H-imidazo[1,5-a][1,2,4]triazolo[1,5-d][1,4]benzodiazepine-10-carboxylate (cp. example 21) (7.08 g, 18.9 mmol), NaOH 1N (76 ml, 76 mmol) in ethanol (70 mL) was stirred for 18 h at ambient temperature. The solvent was distilled off (55 mbar, 45° C.) and the resulting light brown suspension was adjusted with aqueous HCl (1 N, 85 mL) to pH=1.5 at 0° C. The suspension was stirred for 1 h at 0° C., filtered off and washed twice with water (total 50 mL). The solid was dried in vacuo at 60° C. affording the title compound (6.65 g, 99%) as a light brown solid. MS: m/e=346.0/348.2 [M+H]$^+$.

b) 3-Bromo-9H-imidazo[1,5-a][1,2,4]triazolo[1,5-d][1,4]-benzodiazepine-10-carboxylic acid methoxy-methyl-amide To a mixture of 3-bromo-9H-imidazo[1,5-a][1,2,4]triazolo[1,5-d][1,4]benzodiazepine-10-carboxylic acid (4.9 g, 14.2 mmol), N,O-dimethylhydroxylamine hydrochloride (2.21 g, 22.7 mmol), N-methylmorpholine (2.3 mL, 22 mmol) and 4-dimethylaminopyridine (170 mg, 1.4 mmol) in dichloromethane (100 mL) and DMF (10 mL) was added at 0° C. 1-(3-dimethylaminopropyl)-3-ethylcarbodiimide hydrochloride (3.26 g, 17.0 mmol). The reaction mixture was stirred for 18 h at ambient temperature. The dichloromethane was distilled off and ice-cold water (100 mL) was added to the residue. The resulting suspension was stirred for 15 min, filtered and washed with water (50 mL). The solid was dried in vacuo affording the title compound (5.06 g, 92%) as an off-white solid. MS: m/e=389.0/391.0 [M+H]$^+$.

c) 1-[3-Bromo-9H-imidazo[1,5-a][1,2,4]triazolo[1,5-d][1,4]-benzodiazepin-10-yl]-propan-1-one To a suspension of 3-bromo-9H-imidazo[1,5-a][1,2,4]triazolo[1,5-d][1,4]benzodiazepine-10-carboxylic acid methoxy-methyl-amide (500 mg, 1.29 mmol) in THF (20 mL) was added ethylmagnesium bromide solution (3 M in THF, 2.6 mL, 7.8 mmol) at −70° C. under a nitrogen atmosphere. The reaction mixture was stirred in a thawing dry ice bath for 3 h. It was cooled to 0° C. and aqueous HCl (1 N, 15 mL) was added dropwise. The resulting mixture was stirred for 5 min at ambient temperature before diluted with dichloromethane (20 mL) and aqueous Na$_2$CO$_3$ (sat., 20 mL). The aqueous layer was extracted with dichloromethane (20 mL) and the combined organic layers were dried over sodium sulfate. Purification of the residue by chromatography (SiO$_2$, heptane:ethyl acetate:dichloromethane=60:20:20 to 30:50:20:) afforded the title compound (91 mg, 20%) as a white solid. MS: m/e=358.1/360.0 (M+H)$^+$.

EXAMPLE 8

Cyclopropyl-[3-bromo-9H-imidazo[1,5-a][1,2,4]triazolo[1,5-d][1,4]benzodiazepin-10-yl]-methanone As described for example 7c) 3-bromo-9H-imidazo[1,5-a][1,2,4]triazolo[1,5-d][1,4]benzodiazepine-10-carboxylic acid methoxy-methyl-amide (500 mg, 1.29 mmol), using cyclopropylmagnesium bromide solution (0.5 M in THF, 7.7 mL, 3.85 mmol) instead of ethylmagnesium bromide solution, was converted to the title compound (294 mg, 62%) which was obtained as a white solid. MS: m/e=370.0/372.1 [M+H]$^+$.

EXAMPLE 9

1-[[3-Fluoro-9H-imidazo[1,5-a][1,2,4]triazolo[1,5-d][1,4]benzodiazepin-10-yl]carbonyl]-2-pyrrolidinone A mixture of 3-fluoro-9H-imidazo[1,5-a][1,2,4]triazolo[1,5-d][1,4]benzodiazepine-10-carboxylic acid (2.00 g, 7.01 mmol) and thionyl chloride (1.53 mL, 21.0 mmol) in benzene (20 mL) was stirred for 2 h at reflux. Further thionyl chloride (1.50 mL, 20.6 mmol) was added and stirring was continued for another 2 h at this temperature. The resulting clear solution was concentrated, the residue dissolved in THF (60 mL) and added dropwise to a solution of N-trimethylsilyl-pyrrolidin-2-one (1.13 g, 7.18 mmol) in THF (20 mL) at 0° C. The reaction mixture was stirred for 1 h at ambient temperature and for 1.5 h at 70° C. The solvent was distilled off and the residue dissolved in dichloromethane, washed with aqueous NaHCO$_3$ (sat.) and water and was dried over odium sulfate. Recrystallisation from methanol afforded the title compound (600 mg, 24%) as a white crystalline solid. MS: m/e=353.1 (M+H)$^+$.

EXAMPLE 10

3-Fluoro-9H-imidazo[1,5-a][1,2,4]triazolo[1,5-d][1,4]benzodiazepine-10-carboxylic acid prop-2-ynylamide To suspension of 3-fluoro-9H-imidazo[1,5-a][1,2,4]triazolo[1,5-d][1,4]benzodiazepine-10-carboxylic acid (500 mg, 1.75 mmol) in DMF (10 mL) was added 1,1'-carbonyl-diimidazole (426 mg, 2.63 mmol). The reaction mixture was stirred for 6 h at 80° C. After cooling to ambient temperature propargylamine (300 μL, 4.38 mmol) was added and stirring was continued for 16 h at this temperature. The mixture was diluted with water (30 mL) and saturated aqueous NaHCO$_3$ (10 mL) and was extracted with ethyl acetate. The combined organic layers were dried over sodium sulfate. Recrystallisation from ethyl acetate afforded the title compound (72 mg, 0.22 mmol) as a white solid. MS: m/e=323.3 [M+H$^+$].

EXAMPLE 11

3-Fluoro-9H-imidazo[1,5-a][1,2,4]triazolo[1,5-d][1,4]benzodiazepine-10-carboxylic acid benzylamide As described for example 10, 3-fluoro-9H-imidazo[1,5-a][1,2,4]triazolo[1,5-d][1,4]benzo-diazepine-10-carboxylic acid (500 mg, 1.75 mmol), using benzylamine instead of propargylamine, was converted to the title compound (540 mg, 82%) which was obtained as an white solid. MS: m/e=375.3 [M+H$^+$].

EXAMPLE 12

Ethyl 3-cyclopropyl-9H-imidazo[1,5-a][1,2,4]triazolo[1,5-d][1,4]benzodiazepine-10-carboxylate A suspension of ethyl 3-bromo-9H-imidazo[1,5-a][1,2,4]triazolo[1,5-d][1,4]benzodiazepine-10-carboxylate (example 23) (200 mg, 0.53 mmol) in THF (10 mL) was heated to 65° C. To the resulting solution were added tetrakis(triphenylphosphine)palladium(0) (31 mg, 0.03 mmol) and cyclopropylzinc bromide solution (0.38 M in THF, 3.5 mL, 1.3 mmol) and the reaction mixture was stirred for 1 h at 65° C. It was diluted with water (5 mL) and acidified to pH=1 with aqueous HCl (1 N). The THF was distilled off, toluene (5 mL) was added and the mixture stirred for 30 min at ambient temperature before filtered and washed with water. Purification of the residue by chromatography (SiO$_2$, heptane:ethyl acetate:dichloromethane=60:20:20 to 30:50:20:) afforded the title compound (61 mg, 37%) as a white solid. MS: m/e=336.3 (M+H)$^+$.

EXAMPLE 13

Ethyl 3-bromo-6-methyl-9H-imidazo[1,5-a][1,2,4]triazolo[1,5-d][1,4]benzodiazepine-10-carboxylate a) 3-Bromo-2-methyl-6H-[1,2,4]triazolo[1,5-c]quinazolin-5-one As described for example 23b) 4-bromo-2-cyano-phenyl)-carbamic acid ethyl ester (30.0 g, 111 mmol), using acetic acid hydrazide instead of formylhydrazine, was converted to the title compound (28.5 g, 91%) which was obtained as an off-white solid. MS: m/e=277.0/279.1 [M−H]$^-$.

b) 4-Bromo-2-(5-methyl-2H-[1,2,4]triazol-3-yl)-phenylamine

As described for example 23c) 9-bromo-2-methyl-6H-[1,2,4]triazolo[1,5-c]quinazolin-5-one (28.5 g, 102 mmol), instead of 9-bromo-6H-[1,2,4]triazolo[1,5-c]quinazolin-5-one, was converted to the title compound (25.5 g, 99%) which was obtained as an off-white solid. MS: m/e=251.0/253.1 [M−H]$^-$.

c) 9-Bromo-2-methyl-6H-1,3,3a,6-tetraaza-benzo[e]azulen-5-one

As described for example 23d) 4-bromo-2-(5-methyl-2H-[1,2,4]triazol-3-yl)-phenylamine (24.9 g, 98.3 mmol), instead of 4-bromo-2-(2H-[1,2,4]triazol-3-yl)-phenylamine, was converted to the title compound (17.0 g, 59%) which was obtained as an off-white solid. MS: m/e=291.0/293.2 [M−H]$^-$.

d) Ethyl 3-bromo-6-methyl-9H-imidazo[1,5-a][1,2,4]triazolo[1,5-d][1,4]-benzodiazepine-10-carboxylate As described for example 23e) 9-bromo-2-methyl-6H-1,3,3a,6-tetraaza-benzo[e]azulen-5-one (16.8 g, 57.3 mmol) instead of 9-bromo-6H-1,3,3a,6-tetraaza-benzo[e]azulen-5-one was converted to the title compound (14.7 g, 66%) which was obtained as an off-white solid. MS: m/e=388.2/390.1 [M+H]$^+$.

EXAMPLE 14

Ethyl 3-methoxy-9H-imidazo[1,5-a][1,2,4]triazolo[1,5-d][1,4]benzodiazepine-10-carboxylate a) 3-Methoxy-9H-imidazo[1,5-a][1,2,4]triazolo[1,5-d][1,4]-benzodiazepine-10-carboxylic acid To a solution of ethyl 3-fluoro-9H-imidazo[1,5-a][1,2,4]triazolo[1,5-d][1,4]benzodiazepine-10-carboxylate (200 mg, 0.64 mmol) in DMSO (2 mL) was added sodium methoxide (103 mg, 1.92 mmol). The reaction mixture was stirred for 18 h at 60° C. and 24 h at 150° C. Further sodium methoxide (103 mg, 1.92 mmol) was added and stirring was continued for another 24 h at 150° C. The mixture was poured onto ice (30 g), was saturated with sodium chloride and was extracted with ethyl acetate. The combined organic layers were washed with brine. Drying over sodium sulfate afforded the title compound (100 mg, 53%) as a light brown solid. MS: m/e=296.3 $[M+H]^+$.

b) Ethyl 3-methoxy-9H-imidazo[1,5-a][1,2,4]triazolo[1,5-d][1,4]-benzodiazepine-10-carboxylate To a suspension of 3-methoxy-9H-imidazo[1,5-a][1,2,4] triazolo[1,5-d][1,4]benzodiazepine-10-carboxylic acid (81 mg, 0.27 mmol) in ethanol (10 mL) was added sulfuric acid (73 L, 1.36 mmol) and the mixture was stirred for 48 h at 80° C. under a nitrogen atmosphere. It was concentrated, aqueous $Na_2CO_3$ (sat., 10 mL) added and extracted with ethyl acetate. It was dried over sodium sulfate and concentrated. The residue was dissolved in ethyl acetate (5 mL) and heptane (5 mL) was added. The resulting solid was filtered. Recrystallisation from ethyl acetate:heptane (1:1) afforded the title compound (21 mg, 24%) as a white solid. MS: m/e=326.2 $[M+H]^+$.

EXAMPLE 15

Ethyl 3-chloro-6-methyl-9H-imidazo[1,5-a][1,2,4] triazolo[1,5-d][1,4]benzodiazepine-10-carboxylate a) 4-Chloro-2-cyano-phenyl)-carbamic acid ethyl ester As described for example 23a) 2-amino-5-chlorobenzonitrile (33.4 g, 219 mmol), instead of 2-amino-5-bromobenzonitrile, was converted to the title compound (46.9 g, 95%) which was obtained as a light yellow solid. MS: m/e=242.3 $[M+NH_4]^+$.

b) 9-Chloro-2-methyl-6H-[1,2,4]triazolo[1,5-c] quinazolin-5-one

As described for example 23b) 4-chloro-2-cyano-phenyl)-carbamic acid ethyl ester (10.0 g, 44.5 mmol), instead of 4-bromo-2-cyano-phenyl)-carbamic acid ethyl ester, using acetic acid hydrazide instead of formylhydrazine, was converted to the title compound (9.81 g, 94%) which was obtained as a light yellow solid. MS: m/e=234.9 $[M]^+$.

c) 4-Chloro-2-(5-methyl-2H-[1,2,4]triazol-3-yl)-phenylamine

As described for example 23c) 9-chloro-2-methyl-6H-[1, 2,4]triazolo[1,5-c]quinazolin-5-one (9.67 g, 41.2 mmol), instead of 9-bromo-6H-[1,2,4]triazolo[1,5-c]quinazolin-5-one, was converted to the title compound (6.57 g, 76%) which was obtained as an off-white solid. MS: m/e=209.0 $[M+H]^+$.

d) 9-Chloro-2-methyl-6H-1,3,3a,6-tetraaza-benzo[e] azulen-5-one

As described for example 23d) 4-chloro-2-(5-methyl-2H-[1,2,4]triazol-3-yl)-phenylamine (9.44 g, 30.9 mmol), instead of 4-bromo-2-(2H-[1,2,4]triazol-3-yl)-phenylamine, was converted to the title compound (4.83 g, 63%) which was obtained as a white solid. MS: m/e=248.9 $[M]^+$.

e) Ethyl 3-chloro-6-methyl-9H-imidazo[1,5-a][1,2,4] triazolo[1,5-d][1,4]benzodiazepine-10-carboxylate As described for example 23e) 9-chloro-2-methyl-6H-1,3, 3a,6-tetraaza-benzo[e]azulen-5-one (2.49 g, 10.0 mmol) instead of 9-bromo-6H-1,3,3a,6-tetraaza-benzo[e]azulen-5-one was converted to the title compound (1.19 g, 35%) which was obtained as a light brown solid. MS: m/e=344.0 $[M+H]^+$.

EXAMPLE 16

Ethyl 3-chloro-6-(4-fluorophenyl)-9H-imidazo[1,5-a][1,2,4]triazolo[1,5-d][1,4]benzodiazepine-10-carboxylate a) 9-Chloro-2-(4-fluorophenyl)-6H-[1,2,4]triazolo[1, 5-c]quinazolin-5-one As described for example 23b) 4-chloro-2-cyano-phenyl)-carbamic acid ethyl ester (5.00 g, 22.3 mmol), instead of 4-bromo-2-cyano-phenyl)-carbamic acid ethyl ester, using 4-fluorbenzhydrazide instead of formylhydrazine, was converted to the title compound (6.90 g, 98%) which was obtained as a light yellow solid. MS: m/e=315.1 $[M+H]^+$.

b) 4-Chloro-2-(4-fluorophenyl)-2H-[1,2,4]triazol-3-yl)-phenylamine

As described for example 23c) 9-chloro-2-(4-fluorophenyl)-6H-[1,2,4]triazolo[1,5-c]quinazolin-5-one (6.82 g, 21.7 mmol), instead of 9-bromo-6H-[1,2,4]triazolo[1,5-c]quinazolin-5-one, was converted to the title compound (3.98 g, 64%) which was obtained as a light yellow solid. MS: m/e=289.0 $[M+H]^+$.

c) 9-Chloro-2-(4-fluorophenyl)-6H-1,3,3a,6-tetraaza-benzo[e]azulen-5-one

As described for example 23d) 4-chloro-2-(5-(4-fluorophenyl)-2H-[1,2,4]triazol-3-yl)-phenylamine (3.91 g, 13.6 mmol), instead of 4-bromo-2-(2H-[1,2,4]triazol-3-yl)-phenylamine, was converted to the title compound (2.97 g, 67%) which was obtained as an off-white solid. MS: m/e=329.0 $[M+H]^+$.

d) Ethyl 3-chloro-6-(4-fluorophenyl)-9H-imidazo[1, 5-a][1,2,4]triazolo[1,5-d][1,4]benzodiazepine-10-carboxylate As described for example 23e) 9-chloro-2-(4-fluorophenyl)-6H-1,3,3a,6-tetraaza-benzo[e]azulen-5-one (2.86 g, 8.69 mmol) instead of 9-bromo-6H-1,3,3a,6-tetraaza-benzo [e]azulen-5-one was converted to the title compound (63 mg, 1.7%) which was obtained as a light yellow solid. MS: m/e=424.1 $[M+H]^+$.

EXAMPLE 17

Ethyl 3-chloro-6-(3,4-dimethoxyphenyl)-9H-imidazo [1,5-a][1,2,4]triazolo[1,5-d][1,4]benzodiazepine-10-carboxylate a) 9-Chloro-2-(3,4-dimethoxyphenyl)-6H-[1,2,4] triazolo[1,5-c]quinazolin-5-one As described for example 23b) 4-chloro-2-cyano-phenyl)-carbamic acid ethyl ester (5.00 g, 22.3 mmol), instead of 4-bromo-2-cyano-phenyl)-carbamic acid ethyl ester, using 3,4-dimethoxybenzhydrazide instead of formylhydrazide, was converted to the title compound (7.55 g, 95%) which was obtained as a light yellow solid. MS: m/e=375.4 [M–H]⁻.

b) 4-Chloro-2-(3,4-dimethoxyphenyl)-2H-[1,2,4]triazol-3-yl)-phenylamine

As described for example 23c) 9-chloro-2-(3,4-dimethoxyphenyl)-6H-[1,2,4]triazolo[1,5-c]quinazolin-5-one (7.37 g, 20.7 mmol), instead of 9-bromo-6H-[1,2,4]triazolo[1,5-c]quinazolin-5-one, was converted to the title compound (6.24 g, 91%) which was obtained as a light yellow solid. MS: m/e=331.2 [M+H]⁺.

c) 9-Chloro-2-(3,4-dimethoxyphenyl)-6H-1,3,3a,6-tetraaza-benzo[e]azulen-5-one As described for example 23d) 4-chloro-2-(5-(3,4-dimethoxyphenyl)-2H-[1,2,4]triazol-3-yl)-phenylamine (6.18 g, 18.7 mmol), instead of 4-bromo-2-(2H-[1,2,4]triazol-3-yl)-phenylamine, was converted to the title compound (5.06 g, 73%) which was obtained as an off-white solid. MS: m/e=371.0 [M+H]⁺.

d) Ethyl 3-chloro-6-(3,4-dimethoxyphenyl)-9H-imidazo[1,5-a][1,2,4]triazolo[1,5-d][1,4]benzodiazepine-10-carboxylate As described for example 23e) 9-chloro-2-(3,4-dimethoxyphenyl)-6H-1,3,3a,6-tetraaza-benzo[e]azulen-5-one (3.71 g, 10.0 mmol) instead of 9-bromo-6H-1,3,3a,6-tetraaza-benzo[e]azulen-5-one was converted to the title compound (2.24 g, 48%) which was obtained as a light brown solid. MS: m/e=466.2 [M+H]⁺.

EXAMPLE 18

Ethyl 3-acetylamino-9H-imidazo[1,5-a][1,2,4]triazolo[1,5-d][1,4]benzodiazepine-10-carboxylate a) Ethyl 3-amino-9H-imidazo[1,5-a][1,2,4]triazolo[1,5-d][1,4]benzodiazepine-10-carboxylate As described for example 23e) 9-amino-6H-1,3,3a,6-tetraaza-benzo[e]azulen-5-one (8.60 g, 40.0 mmol), instead of 9-bromo-6H-1,3,3a,6-tetraaza-benzo[e]azulen-5-one, was converted to the title compound which was obtained as a white solid. MS: m/e=311.2 [M+H]⁺.

b) Ethyl 3-acetylamino-9H-imidazo[1,5-a][1,2,4]triazolo[1,5-d][1,4]-benzodiazepine-10-carboxylate To a solution of 3-amino-9H-imidazo[1,5-a][1,2,4]triazolo[1,5-d][1,4]benzodiazepine-10-carboxylate (310 mg, 1.00 mmol) in pyridine (30 mL) was added dropwise at 10° C. acetic anhydride (0.50 mL, 5.29 mmol) and the reaction mixture was stirred at ambient temperature for 24 h. The resulting solid was filtered and washed with toluene. Recrystallisation from ethyl acetate provided the title compound (260 mg, 74%) as a white crystalline solid. MS: m/e=353.2 [M+H]⁺.

EXAMPLE 19

Ethyl 3-trifluoromethoxy-9H-imidazo[1,5-a][1,2,4]triazolo[1,5-d][1,4]benzodiazepine-10-carboxylate a) 2-Amino-5-trifluoromethoxybenzonitrile

To a solution of 2-bromo-4-(trifluoromethoxy)aniline (15.1 g, 60.0 mmol) in N-methylpyrrolidone (100 mL) was added copper cyanide (10.6 g, 118 mmol) and the reaction mixture was stirred for 6.5 h at 163° C. After cooling to ambient temperature it was poured onto ice-water (300 mL) and aqueous ammonia (350 mL). The resulting brown precipitate was collected by filtration, washed with water (150 mL) and dissolved in dichloromethane (350 mL). The insoluble material was removed by filtration and the filtrate was washed with brine (100 mL) and dried over sodium sulfate. Purification by chromatography (SiO₂, heptane:ethyl acetate=95:5 to 25:75:) afforded the title compound (9.09 g, 76%) as a brown solid. MS: m/e=405.1 [2M+H]⁺.

b) (2-Cyano-4-trifluoromethoxy-phenyl)-carbamic acid ethyl ester

As described for example 23a) 2-amino-5-trifluoromethoxybenzonitrile (8.89 g, 44.0 mmol), instead of 2-amino-5-bromobenzonitrile, was converted to the title compound (8.53 g, 71%) which was obtained as a yellow solid. MS: m/e=275.2 [M+H]⁺.

c) 9-Trifluoromethoxy-6H-[1,2,4]triazolo[1,5-c]quinazolin-5-one

As described for example 23b) (2-cyano-4-trifluoromethoxy-phenyl)-carbamic acid ethyl ester (8.31 g, 30.3 mmol), instead of (4-bromo-2-cyano-phenyl)-carbamic acid ethyl ester, was converted to the title compound (5.63 g, 69%) which was obtained as a yellow solid. MS: m/e=271.2 [M+H]⁺.

d) 4-Trifluoromethoxy-2-(2H-[1,2,4]triazol-3-yl)-phenylamine

As described for example 23c) 9-trifluoromethoxy-6H-[1,2,4]triazolo[1,5-c]quinazolin-5-one (5.51 g, 20.4 mmol), instead of 9-bromo-6H-[1,2,4]triazolo[1,5-c]quinazolin-5-one, was converted to the title compound (3.22 g, 65%) which was obtained as a light brown solid. MS: m/e=245.2 [M+H]⁺.

e) 2-Chloro-N-[2-(2H-[1,2,4]triazol-3-yl)-4-trifluoromethoxy-phenyl]-acetamide To a cooled solution of 4-trifluoromethoxy-2-(2H-[1,2,4]triazol-3-yl)-phenylamine (3.00 g, 12.3 mmol) in acetic acid (62 mL) was added dropwise chloroacetyl chloride (1.96 mL, 24.6 mmol). The resulting light brown suspension was stirred for 20 h at ambient temperature and was then poured into water (246 mL) and stirred for another 3 h. The precipitate was filtered off and washed with water. Drying in vacuo afforded the title compound (3.22 g, 82%) as an off-white solid. MS: m/e=323.1 [M+H]⁺.

f) 9-Trifluoromethoxy-6H-1,3,3a,6-tetraaza-benzo[e]azulen-5-one

To a solution of 2-chloro-N-[2-(2H-[1,2,4]triazol-3-yl)-4-trifluoromethoxy-phenyl]-acetamide (3.15 g, 9.82 mmol) in dioxane (100 mL) was added aqueous sodium hydroxide (32%, 2.18 mL, 23.6 mmol) and the reaction mixture was stirred for 19 h at ambient temperature. It was poured onto aqueous ammonium chloride (1M, 50 mL) and the organic solvent was removed by destillation. The resulting suspension was filtered and the solid was washed with ice-cold water (50 mL). Drying in vacuo afforded the title compound (682 mg, 24%) as a light yellow solid. MS: m/e=285.0 [M+H]⁺.

g) 5-[1,2,4]-Triazol-1-yl-9-trifluoromethoxy-4H-1,3, 3a,6-tetraaza-benzo[e]azulene To a solution of 1,2,4-triazole (1.00 g, 14.5 mmol) and N-ethyldiisopropylamine (2.64 mL, 15.4 mmol) in acetonitrile (13 mL) was added dropwise phosphorous oxychloride (0.40 mL, 4.40 mmol) at 0° C. The solution was stirred for 2 h at 0° C. before 5-[1,2,4]triazol-1-yl-9-trifluoromethoxy-4H-1,3,3a,6-tetraaza-benzo[e]azulene (625 mg, 2.20 mmol) was added and stirring was continued for 20 h at 90° C. The reaction mixture was cooled to ambient temperature and poured onto ice-water, stirred for 15 min and was filtered off. Washing with water and drying in vacuo afforded the title compound (357 mg, 48%) as a light brown solid. MS: m/e=336.2 [M+H]$^+$.

h) Ethyl 3-trifluoromethoxy-9H-imidazo[1,5-a][1,2, 4]triazolo[1,5-d][1,4]-benzodiazepine-10-carboxylate To a solution of potassium tert-butylate (156 mg, 1.39 mmol) in DMF (3.3 mL) was added dropwise ethyl isocyanoacetate (177 mg, 14.9 mmol) over a period of 1 min at −50° C. The reaction mixture was stirred for 1 h at this temperature before 5-[1,2,4]triazol-1-yl-9-trifluoromethoxy-4H-1,3,3a,6-tetraaza-benzo[e]azulene (333 mg, 1 mmol) was added in one portion. After stirring for 30 min at −50° C., the reaction mixture was allowed to warm to ambient temperature stirred for 1.5 h. Acetic acid (0.34 mL, 59.6 mmol) was added at 0° C. and the mixture was stirred for another 30 min before poured into ice-water and filtered off and washed with water. Purification by chromatography (SiO$_2$, heptane:ethyl acetate:dichloromethane=75:15:10 to 0:90:10) afforded the title compound (72 mg, 19%) as a white solid. MS: m/e=380.1 [M+H]$^+$.

EXAMPLE 20

3-Bromo-9H-imidazo[1,5-a][1,2,4]triazolo[1,5-d][1, 4]benzodiazepine-10-carbaldehyde a) 3-Bromo-10-hydroxymethyl-9H-imidazo[1,5-a][1, 2,4]triazolo[1,5-d][1,4]benzodiazepine As described for example 3a, ethyl 3-bromo-9H-imidazo[1,5-a][1,2,4]triazolo[1,5-d][1,4]benzodiazepine-10-carboxylate (cp. Example 23) (1.03 g, 2.75 mmol), instead of ethyl 3-fluoro-9H-imidazo[1,5-a][1,2,4]triazolo[1,5-d][1,4] benzodiazepine-10-carboxylate, was converted to the title compound (652 mg, 71%) which was obtained as a white solid. MS: m/e=332.1/334.1 (M+H$^+$).

b) 3-Bromo-9H-imidazo[1,5-a][1,2,4]triazolo[1,5-d] [1,4]benzodiazepine-10-carbaldehyde As described for example 2a, 3-bromo-10-hydroxymethyl-9H-imidazo[1,5-a][1,2,4]triazolo[1,5-d][1,4]benzodiazepine (600 mg, 1.81 mmol), instead of 3-chloro-10-hydroxymethyl-9H-imidazo[1,5-a][1,2,4]triazolo[1,5-d][1,4] benzodiazepine, was converted to the title compound (208 mg, 35%) which was obtained as a white solid. MS: m/e=330.1/332.1 (M+H$^+$).

EXAMPLE 21

3-Chloro-9H-imidazo[1,5-a][1,2,4]triazolo[1,5-d][1, 4]benzodiazepine-10-carbaldehyde a) 3-Chloro-10-hydroxymethyl-9H-imidazo[1,5-a][1, 2,4]triazolo[1,5-d][1,4]benzodiazepine To a suspension of ethyl 3-chloro-9H-imidazo[1,5-a][1,2, 4]triazolo[1,5-d][1,4]benzodiazepine-10-carboxylate[1] (10.0 g, 30.3 mmol) in THF (400 mL) was added lithium borohydride (800 mg, 34.9 mmol) and the reaction mixture was heated to reflux for 7 hrs. After cooling to ambient temperature, it was acidified to pH=2 by adding aq HCl (1 N) and diluted with water (50 mL). The solvent was evaporated and the residue was taken in aq. NH$_4$OH (conc., 100 mL). The resulting solid were filtered off, washed with water (3×10 mL) and dried (60° C., vacuo) affording the title compound (4.01 g, 45.8%) as a white solid. MS: m/e=287.9 (M$^+$).

b) 3-Chloro-9H-imidazo[1,5-a][1,2,4]triazolo[1,5-d] [1,4]-benzodiazepine-10-carbaldehyde To a solution of 3-chloro-10-hydroxymethyl-9H-imidazo [1,5-a][1,2,4]triazolo[1,5-d][1,4]benzodiazepine (15.0 g, 52.1 mmol) in dichloromethane (1.5 L) was added manganese(IV) oxide (188 g; 1.94 mol) and the mixture was stirred at ambient temperature for 24 h. It was filtered over dicalite, washed with dichloromethane and concentrated. The residue was dissolved in dichloromethane (700 mL) at 40° C. and ethyl acetate (100 mL) was added. The product started to crystallise. After cooling the dichloromethane was evaporated and the solid filtered. Drying in vacuo afforded the title compound (11.8 g, 79.2%) as a yellow crystalline solid. MS: m/e=286.1 (M+H$^+$).

EXAMPLE 22

Ethyl 3-chloro-6-phenyl-9H-imidazo[1,5-a][1,2,4] triazolo[1,5-d][1,4]benzodiazepine-10-carboxylate a) 9-Chloro-2-phenyl-6H-[1,2,4]triazolo[1,5-c] quinazolin-5-one As described for example 23b) 4-chloro-2-cyano-phenyl)-carbamic acid ethyl ester (5.00 g, 22.3 mmol), instead of 4-bromo-2-cyano-phenyl)-carbamic acid ethyl ester, using benzhydrazide instead of formylhydrazine, was converted to the title compound (6.50 g, 98%) which was obtained as a light yellow solid. MS: m/e=297.1 [M+H]$^+$.

b) 4-Chloro-2-phenyl-2H-[1,2,4]triazol-3-yl)-phenylamine

As described for example 23c) 9-chloro-2-phenyl-6H-[1, 2,4]triazolo[1,5-c]quinazolin-5-one (6.34 g, 21.4 mmol), instead of 9-bromo-6H-[1,2,4]triazolo[1,5-c]quinazolin-5-one, was converted to the title compound (5.35 g, 92%) which was obtained as a light yellow solid. MS: m/e=271.0 [M+H]$^+$.

c) 9-Chloro-2-phenyl-6H-1,3,3a,6-tetraaza-benzo[e] azulen-5-one

As described for example 23d) 4-chloro-2-(5-phenyl-2H-[1,2,4]triazol-3-yl)-phenylamine (5.24 g, 19.3 mmol), instead of 4-bromo-2-(2H-[1,2,4]triazol-3-yl)-phenylamine, was converted to the title compound (4.40 g, 73%) which was obtained as an off-white solid. MS: m/e=311.0 [M+H]$^+$.

d) Ethyl 3-chloro-6-phenyl-9H-imidazo[1,5-a][1,2,4]triazolo[1,5-d][1,4]-benzodiazepine-10-carboxylate As described for example 23e) 9-chloro-2-phenyl-6H-1,3,3a,6-tetraaza-benzo[e]azulen-5-one (3.11 g, 10.0 mmol) instead of 9-bromo-6H-1,3,3a,6-tetraaza-benzo[e]azulen-5-one was converted to the title compound (1.26 g, 31%) which was obtained as a light yellow solid. MS: m/e=424.1 [M+NH$_4$]$^+$.

EXAMPLE 23

Ethyl 3-bromo-9H-imidazo[1,5-a][1,2,4]triazolo[1,5-d][1,4]benzodiazepine-10-carboxylate a) 4-Bromo-2-cyano-phenyl)-carbamic acid ethyl ester

A suspension of 2-amino-5-bromobenzonitrile (58.5 g, 297 mmol) in ethyl chloroformate (141 ml, 1.48 mol) was heated at reflux for 5 h. The excess ethyl chloroformate (99 mL) was distilled off and toluene (96 mL) was added. Slow addition of cyclohexane (228 mL) induced crystallization. The resulting solid was collected by filtration and rinsed with cyclohexane. Drying in vacuo afforded the title compound (54.3 g, 68%) as an orange solid. MS: m/e=267.1/269.2 [M−H]$^-$.

b) 9-Bromo-6H-[1,2,4]triazolo[1,5-c]quinazolin-5-one

To a solution of 4-bromo-2-cyano-phenyl)-carbamic acid ethyl ester (40.4 g, 150 mmol) in NMP (170 mL) was added formylhydrazine (10.0 g, 150 mmol). The resulting mixture was stirred for 1.5 h at 160° C. under a gentle nitrogen sweep. It was cooled to below 100° C. and water (340 mL) was added slowly. The resulting slurry was cooled to 25° C. and stirred for 15 min. The solid was collected by filtration and washed with water and 2-propanol. Drying in vacuo afforded the title compound (32.4 g, 81%) as a light yellow solid. MS: m/e=264.9/267.0 [M+H$^+$].

c) 4-Bromo-2-(2H-[1,2,4]triazol-3-yl)-phenylamine

To a well stirred slurry of 9-bromo-6H-[1,2,4]triazolo[1,5-c]quinazolin-5-one (32.0 g, 171 mmol) in ethylene glycol (146 mL) which was heated at 100° C., was added aqueous NaOH (32%, 22.4 ml, 241 mmol). The slurry was heated at 140° C. for 17.5 h. The resulting solution was cooled to 27° C. and the product began to crystallize. Water (146 mL) and 1-octanol (1.73 mL) were added and the pH of the suspension was adjusted to 6.5 by the slow addition of glacial acetic acid (14 mL). The resulting slurry was stirred for 30 min, the solid was collected by filtration and washed with water and 2-propanol. Drying in vacuo afforded the title compound (25.2 g, 87%) as a light yellow solid. MS: m/e=239.0/241.1 [M+H$^+$].

d) 9-Bromo-6H-1,3,3a,6-tetraaza-benzo[e]azulen-5-one

A solution of 4-bromo-2-(2H-[1,2,4]triazol-3-yl)-phenylamine (25.0 g, 105 mmol) in dioxane (870 mL) and pyridine (10.0 mL) was cooled to 12° C. A solution of chloroacetyl chloride (9.56 ml, 121 mmol) in diethylether (34.7 mL) was added dropwise over a period of 8 min. The mixture was stirred at 10° C.-12° C. for 75 min and treated within 5 min with aqueous NaOH (2 N, 126 ml, 251 mmol). The mixture was stirred for 17.5 h at ambient temperature. The pH thereby dropped to about pH=9 and it was adjusted to pH=8 with HCl (3 N, 6 mL). After evaporation the residue was stirred at 15° C. for 30 min in water (650 mL) and ethyl acetate (22 mL). The crystals were filtered off, washed with cold water and dried in vacuo. Trituration in ethyl acetate (100 mL) afforded the title compound (13.4 g, 46%) as a light yellow solid. MS: m/e=279.0/281.0 [M+H]$^+$.

e) Ethyl 3-bromo-9H-imidazo[1,5-a][1,2,4]triazolo[1,5-d][1,4]-benzodiazepine-10-carboxylate To a suspension of 9-bromo-6H-1,3,3a,6-tetraaza-benzo[e]azulen-5-one (10.7 g, 38.5 mmol) in chloroform (270 ml, filtrated over Alox basic) was added N,N-dimethyl-p-toluidine (13.9 ml, 96.1 mmol) and phosphorous oxychloride (5.28 ml, 57.7 mmol). The mixture was stirred for 22 h at reflux, then cooled to 30° C. and poured into aq NaHCO$_3$ (10%, 575 mL). After extraction with chloroform (50 mL) the organic layers were dried over sodium sulfate and concentrated. In the meantime potassium tert-butylate (4.31 g, 38.5 mmol) was added in portions to a solution of ethyl isocyanoacetate (4.42 ml, 38.5 mmol) in THF (115 mL) at −25° C. to −10° C. The resulting suspension was stirred for 45 min at −10° C. and then cooled to −65° C. The solution from above was added dropwise within 10 min and the mixture was stirred for 16 h at ambient temperature. Acetic acid (1.6 mL) was added, stirred for 15 min and then poured into aq NaHCO$_3$ (5%, 460 mL) and ethyl acetate (96 mL). The resulting crystals were filtered off, washed with ethyl acetate (25 mL), water (50 mL) and ethyl acetate (25 mL). Drying in vacuo afforded the title compound (4.81 g, 33%) as a light brown solid. MS: m/e=373.7/375.7 [M]$^+$.

EXAMPLE 24

Ethyl 3-ethynyl-9H-imidazo[1,5-a][1,2,4]triazolo[1,5-d][1,4]benzodiazepine-10-carboxylate a) Ethyl 3-trimethylsilanylethynyl-9H-imidazo[1,5-a][1,2,4]triazolo[1,5-d][1,4]-benzodiazepine-10-carboxylate A suspension of ethyl 3-bromo-9H-imidazo[1,5-a][1,2,4]triazolo[1,5-d][1,4]benzodiazepine-10-carboxylate (Example 23) (374 mg, 1.00 mmol), trimethylsilylacetylene (221 µl, 1.55 mmol), bis(triphenylphosphine)palladium (II) chloride (35 mg, 0.05 mmol), triphenylphosphine (8 mg, 0.03 mmol) and triethylamine (500 µl, 3.60 mmol) in THF (5 ml) was stirred for 15 min at ambient temperature. Then cuprous bromide (1.4 mg, 0.01 mmol) was added and the reaction mixture was stirred for 21 h at 70° C. under an argon atmosphere. It was diluted with ethyl acetate (20 ml) and washed with aqueous citric acid (10%, 40 ml). The aqueous layer was extracted with ethyl acetate (40 ml) and the combined organic layers were dried over sodium sulfate and evaporated. Purification by chromatography (SiO$_2$, heptane:ethyl acetate:dichloromethane:methanol=75:15:10:0 to 0:80:10:10) afforded the title compound (245 mg, 63%) as a yellow foam. MS: m/e=392.2 [M+H]$^+$.

b) Ethyl 3-ethynyl-9H-imidazo[1,5-a][1,2,4]triazolo[1,5-d][1,4]-benzodiazepine-10-carboxylate To a solution of ethyl 3-trimethylsilanylethynyl-9H-imidazo[1,5-a][1,2,4]triazolo[1,5-d][1,4]benzodiazepine-10- carboxylate (196 mg, 0.50 mmol) in THF (1.8 ml) and methanol (0.18 ml) was added tetrabutylammonium fluoride trihydrate (166 mg, 0.74 mmol) at −70° C. After stirring for 30 min at this temperature the dry ice bath was replaced by an ice bath. After additional 1.5 h stirring, the mixture was diluted with ethyl acetate (10 ml) and was washed with aqueous sodium hydrogencarbonate (saturated). The aqueous layers were extracted with ethyl acetate and the combined organic layers were dried over sodium sulfate and evaporated. Purification by chromatography ($SiO_2$, heptane:ethyl acetate: dichloromethane:methanol=75:15:10:0 to 0:80:10:10) afforded the title compound (135 mg, 84%) as a white solid. MS: m/e=320.0 $[M+H]^+$.

EXAMPLE 25

2-Methoxy-ethyl 3-bromo-9H-imidazo[1,5-a][1,2,4]triazolo[1,5-d][1,4]benzodiazepine-10-carboxylate To a mixture of sodium dihydro-bis(2-methoxyethoxy)aluminate (3.5 M in toluene, 0.19 ml, 0.67 mmol) in toluene (2 ml) was added dropwise at 0° C. 1-methyl-2-pyrrolidone (0.08 ml, 0.75 mmol) and stirred for 30 min at this temperature. This solution was added at 0° C. to a mixture of ethyl 3-bromo-9H-imidazo[1,5-a][1,2,4]triazolo[1,5-d][1,4]benzodiazepine-10-carboxylate (cp. Example 23) (200 mg, 0.54 mmol) in toluene (2 ml) and the resulting mixture was stirred for 2 h at ambient temperature. It was concentrated in vacuo and stirred for 18 h in THF (5 ml). Further aluminate solution (to a mixture of sodiumdihydro-bis(2-methoxyethoxy)aluminate solution (3.5 M in toluene, 0.38 ml, 1.34 mmol) in THF (2 ml) was added dropwise at 0° C. 1-methyl-2-pyrrolidone (0.17 ml, 0.75 mmol) and stirred for 30 min at 0° C.) was added and stirring was continued for 3 d at ambient temperature. The mixture was quenched with aqueous HCl (1 N, 10 ml) and stirred for 30 min at 65° C. After cooling to 0° C. aqueous sodium carbonate (saturated, 10 ml) was added and it was extracted with ethyl acetate (20 ml). The organic layers were washed with brine, dried over sodium sulfate and were evaporated. Purification by chromatography ($SiO_2$, heptane: ethyl acetate:dichloromethane=60:20:20 to 30:50:20) afforded the title compound (40 mg, 19%) as a white solid. MS: m/e=404.3/406.2 $[M+H]^+$.

EXAMPLE 26

1-[3-Bromo-9H-imidazo[1,5-a][1,2,4]triazolo[1,5-d][1,4]benzodiazepin-10-yl]-butan-1-one To a solution of 3-bromo-9H-imidazo[1,5-a][1,2,4]triazolo[1,5-d][1,4]benzodiazepine-10-carboxylic acid methoxy-methyl-amide (78 mg, 0.20 mmol) in THF (10 ml) was added propylmagnesium bromide solution (2 M in THF, 0.30 mL, 0.60 mmol) at −78° C. under an argon atmosphere. After 5 min stirring at −78° C., the dry-ice-bath was removed and the reaction mixture was stirred for 4.5 h while allowing to warm to ambient temperature, followed by stirring for 23 h at 40° C. Further grignard-solution (1.60 mmol) was added and stirring continued for another 22 h at 60° C. After cooling to 0° C., aqueous HCl (1 M, 4.0 ml) was added and the mixture stirred for 1 h. Aqueous sodium carbonate (saturated, 8 ml) was added and the mixture was extracted with ethyl acetate. The combined organic layers were washed with water and brine and wereevaporated. Purification by chromatography ($SiO_2$, acetonitril:water:triethylamine=9.5:90:0.5 to 94.5:5: 0.5) afforded the title compound (28 mg, 38%) as an off-white solid. MS: m/e=374.0 $[M+H]^+$.

EXAMPLE 27

1-[3-Bromo-9H-imidazo[1,5-a][1,2,4]triazolo[1,5-d][1,4]benzodiazepin-10-yl]-pentan-1-one As described for example 26,3-bromo-9H-imidazo[1,5-a][1,2,4]triazolo[1,5-d][1,4]benzodiazepine-10-carboxylic acid methoxy-methyl-amide (78 mg, 0.20 mmol), using butylmagnesium chloride solution (2 M in THF, 0.30 mL, 0.60 mmol) instead of propylmagnesium bromide solution, was converted to the title compound (22 mg, 28%) which was obtained as a white solid. MS: m/e=388.0 $[M+H]^+$.

EXAMPLE 28

1-[3-Bromo-9H-imidazo[1,5-a][1,2,4]triazolo[1,5-d][1,4]benzodiazepin-10-yl]-but-2 (E)-en-1-one As described for example 26,3-bromo-9H-imidazo[1,5-a][1,2,4]triazolo[1,5-d][1,4]benzodiazepine-10-carboxylic acid methoxy-methyl-amide (78 mg, 0.20 mmol), using 1-methyl-1-propenylmagnesium bromide solution (0.5 M in THF, 1.20 mL, 0.60 mmol) instead of propylmagnesium bromide solution, was converted to the title compound (23 mg, 30%) which was obtained as a light yellow solid. MS: m/e=383.9 $[M+H]^+$.

EXAMPLE 29

[3-Bromo-9H-imidazo[1,5-a][1,2,4]triazolo[1,5-d][1,4]benzodiazepin-10-yl]-o-tolyl-methanone As described for example 26,3-bromo-9H-imidazo[1,5-a][1,2,4]triazolo[1,5-d][1,4]benzodiazepine-10-carboxylic acid methoxy-methyl-amide (78 mg, 0.20 mmol), using o-tolylmagnesium bromide solution (2 M in diethylether, 0.30 mL, 0.60 mmol) instead of propylmagnesium bromide solution, was converted to the title compound (24 mg, 29%) which was obtained as a light brown solid. MS: m/e=421.9 $[M+H]^+$.

EXAMPLE 30

1-[3-Bromo-9H-imidazo[1,5-a][1,2,4]triazolo[1,5-d][1,4]benzodiazepin-10-yl]-ethanone As described for example 26,3-bromo-9H-imidazo[1,5-a][1,2,4]triazolo[1,5-d][1,4]benzodiazepine-10-carboxylic acid methoxy-methyl-amide (78 mg, 0.20 mmol), using methylmagnesium bromide solution (3 M in diethylether, 0.20 mL, 0.60 mmol) instead of propylmagnesium bromide solution, was converted to the title compound (10 mg, 15%) which was obtained as a light brown solid. MS: m/e=346.0 $[M+H]^+$.

EXAMPLE 31

1-[3-Bromo-9H-imidazo[1,5-a][1,2,4]triazolo[1,5-d][1,4]benzodiazepin-10-yl]-3-methyl-butan-1-one As described for example 26,3-bromo-9H-imidazo[1,5-a][1,2,4]triazolo[1,5-d][1,4]benzodiazepine-10-carboxylic acid methoxy-methyl-amide (78 mg, 0.20 mmol), using iso-butylmagnesium chloride solution (2 M in diethylether, 0.30 mL, 0.60 mmol) instead of propylmagnesium bromide solution, was converted to the title compound (15 mg, 19%) which was obtained as a yellow oil. MS: m/e=388.0 [M+H]$^+$.

EXAMPLE 32

1-[3-Bromo-9H-imidazo[1,5-a][1,2,4]triazolo[1,5-d] [1,4]benzodiazepin-10-yl]-2-phenyl-ethanone As described for example 26,3-bromo-9H-imidazo[1,5-a] [1,2,4]triazolo[1,5-d][1,4]benzodiazepine-10-carboxylic acid methoxy-methyl-amide (78 mg, 0.20 mmol), using benzylmagnesium chloride solution (1 M in diethylether, 0.60 mL, 0.60 mmol) instead of propylmagnesium bromide solution, was converted to the title compound (3 mg, 4%) which was obtained as a yellow oil. MS: m/e=421.9 [M+H]$^+$.

EXAMPLE 33

1-[3-Bromo-9H-imidazo[1,5-a][1,2,4]triazolo[1,5-d] [1,4]benzodiazepin-10-yl]-3-phenyl-propan-1-one As described for example 26,3-bromo-9H-imidazo[1,5-a] [1,2,4]triazolo[1,5-d][1,4]benzodiazepine-10-carboxylic acid methoxy-methyl-amide (78 mg, 0.20 mmol), using phenethylmagnesium chloride solution (1 M in THF, 0.60 mL, 0.60 mmol) instead of propylmagnesium bromide solution, was converted to the title compound (4 mg, 5%) which was obtained as a light brown solid. MS: m/e=436.0 [M+H]$^+$.

EXAMPLE 34

[3-Bromo-9H-imidazo[1,5-a][1,2,4]triazolo[1,5-d][1, 4]benzodiazepin-10-yl]-phenyl-methanone As described for example 26,3-bromo-9H-imidazo[1,5-a] [1,2,4]triazolo[1,5-d][1,4]benzodiazepine-10-carboxylic acid methoxy-methyl-amide (78 mg, 0.20 mmol), using phenylmagnesium bromide solution (1 M in THF, 0.60 mL, 0.60 mmol) instead of propylmagnesium bromide solution, was converted to the title compound (12 mg, 15%) which was obtained as a white solid. MS: m/e=406.1 [M+H]$^+$.

EXAMPLE 35

[3-Bromo-9H-imidazo[1,5-a][1,2,4]triazolo[1,5-d][1, 4]benzodiazepin-10-yl]-thiophen-2-yl-methanone As described for example 26,3-bromo-9H-imidazo[1,5-a] [1,2,4]triazolo[1,5-d][1,4]benzodiazepine-10-carboxylic acid methoxy-methyl-amide (78 mg, 0.20 mmol), using thiophen-2-ylmagnesium bromide solution (2 M in THF, 0.30 mL, 0.60 mmol) instead of propylmagnesium bromide solution, was converted to the title compound (8 mg, 10%) which was obtained as a brown solid. MS: m/e=411.9 [M+H]$^+$.

EXAMPLE 36

1-[3-Bromo-9H-imidazo[1,5-a][1,2,4]triazolo[1,5-d] [1,4]benzodiazepin-10-yl]-2-(3-chloro-phenyl)-ethanone As described for example 26,3-bromo-9H-imidazo[1,5-a] [1,2,4]triazolo[1,5-d][1,4]benzodiazepine-10-carboxylic acid methoxy-methyl-amide (78 mg, 0.20 mmol), using 3-chlorobenzylmagnesium chloride solution (0.25 M in THF, 2.40 mL, 0.60 mmol) instead of propylmagnesium bromide solution, was converted to the title compound (4 mg, 5%) which was obtained as a light yellow solid. MS: m/e=456.1 [M+H]$^+$.

EXAMPLE 37

3-Fluoro-9H-imidazo[1,5-a][1,2,4]triazolo[1,5-d][1, 4]benzodiazepine-10-carboxylic acid cyclopropylamide As described for example 10,3-fluoro-9H-imidazo[1,5-a] [1,2,4]triazolo[1,5-d][1,4]benzo-diazepine-10-carboxylic acid (500 mg, 1.75 mmol), using cyclopropylamine instead of propargylamine, was converted to the title compound (329 mg, 58%) which was obtained as a white solid. MS: m/e=325.3 [M+H]$^+$.

EXAMPLE 38

Ethyl 3-(2,2,2-trifluoro-acetylamino)-9H-imidazo[1, 5-a][1,2,4]triazolo[1,5-d][1,4]benzodiazepine-10-carboxylate To a solution of ethyl 3-amino-9H-imidazo[1,5-a][1,2,4] triazolo[1,5-d][1,4]benzodiazepine-10-carboxylate (150 mg, 0.48 mmol) and N,N-diisopropyl ethyl amine (0.25 mL, 1.44 mmol) in dichloromethane (5 mL) was added dropwise at 15° C. trifluoroacetic anhydride (87 µL, 0.62 mmol). The reaction mixture was stirred for 30 min at ambient temperature before pouring onto aqueous sodium hydrogencarbonate (saturated) and extraction with dichloromethane, drying over sodium sulfate and concentration. Purification of the residue by chromatography (SiO$_2$, dichloromethane:methanol=40:1 to 15:1:) afforded the title compound (175 mg, 89%) as a yellow solid. MS: m/e=407.1 [M+H]$^+$.

EXAMPLE 39

Ethyl 3-isobutyrylamino-9H-imidazo[1,5-a][1,2,4] triazolo[1,5-d][1,4]benzodiazepine-10-carboxylate To a solution of ethyl 3-amino-9H-imidazo[1,5-a][1,2,4] triazolo[1,5-d][1,4]benzodiazepine-10-carboxylate (150 mg, 0.48 mmol) and N,N-diisopropyl ethyl amine (0.25 mL, 1.44 mmol) in dichloromethane (5 mL) was added dropwise at 15° C. isobutyric acid chloride (65 µL, 0.62 mmol). The reaction mixture was stirred for 30 min at ambient temperature before pouring onto aqueous sodium carbonate (saturated) and extraction with dichloromethane, drying over sodium sulfate and concentration. Purification of the residue by chromatography (SiO$_2$, dichloromethane:methanol=40:1 to 15:1:) afforded the title compound (178 mg, 97%) as an off-white solid. MS: m/e=381.1 [M+H]$^+$.

EXAMPLE 40

Ethyl 3-[(isoxazole-5-carbonyl)-amino]-9H-imidazo [1,5-a][1,2,4]triazolo[1,5-d][1,4]benzodiazepine-10-carboxylate As described for example 39, ethyl 3-amino-9H-imidazo [1,5-a][1,2,4]triazolo[1,5-d][1,4]benzodiazepine-10-carboxylate (150 mg, 0.48 mmol), using isoxazole-5-carbonyl chloride instead of isobutyric acid chloride, was converted to the title compound (105 mg, 54%) which was obtained as an off-white solid. MS: m/e=406.2 [M+H]$^+$.

EXAMPLE 41

Ethyl 3-(3-methoxy-propionylamino)-9H-imidazo[1,5-a][1,2,4]triazolo[1,5-d][1,4]benzodiazepine-10-carboxylate As described for example 39, ethyl 3-amino-9H-imidazo[1,5-a][1,2,4]triazolo[1,5-d][1,4]benzodiazepine-10-carboxylate (150 mg, 0.48 mmol), using 3-methoxy-propionyl chloride instead of isobutyric acid chloride, was converted to the title compound (20 mg, 10%) which was obtained as an off-white solid. MS: m/e=397.0 [M+H]$^+$.

EXAMPLE 42

Ethyl 3-formylamino-9H-imidazo[1,5-a][1,2,4]triazolo[1,5-d][1,4]benzodiazepine-10-carboxylate To formic acid (3.04 mL, 81 mmol) is added dropwise acetic anhydride (92 μL, 0.97 mmol) and the reaction mixture is stirred for 1 h at ambient temperature before adding ethyl 3-amino-9H-imidazo[1,5-a][1,2,4]triazolo[1,5-d][1,4]benzodiazepine-10-carboxylate (100 mg, 0.32 mmol). After 2 h stirring at this temperature aqueous sodium hydrogencarbonate (half-saturated) was added and stirring was continued for 30 min. After extraction with dichloromethane/methanol (9:1), the combined organic layers were dried over sodium sulfate and concentrated. Crystallisation from methanol followed by recrystallisation from acetonitrile afforded the title compound (50 mg, 44%) which was obtained as a white solid. MS: m/e=338.9 [M+H]$^+$.

EXAMPLE 43

Ethyl 3-ethoxycarbonylamino-9H-imidazo[1,5-a][1,2,4]triazolo[1,5-d][1,4]benzodiazepine-10-carboxylate As described for example 39, ethyl 3-amino-9H-imidazo[1,5-a][1,2,4]triazolo[1,5-d][1,4]benzodiazepine-10-carboxylate (110 mg, 0.35 mmol), using ethyl chloroformate instead of isobutyric acid chloride, was converted to the title compound (90 mg, 66%) which was obtained as a white solid. MS: m/e=382.2 [M]$^+$.

EXAMPLE 44

Ethyl 3-(3-ethyl-ureido)-9H-imidazo[1,5-a][1,2,4]triazolo[1,5-d][1,4]benzodiazepine-10-carboxylate A mixture of ethyl 3-amino-9H-imidazo[1,5-a][1,2,4]triazolo[1,5-d][1,4]benzodiazepine-10-carboxylate (50 mg, 0.16 mmol), ethyl isocyanate (19 μL, 0.24 mmol) and triethylamine (17 μL, 0.16 mmol) in THF (4 mL) was heated to reflux for 4 h. The reaction mixture was poured onto water and was extracted with dichloromethane, dried over sodium sulfate and concentrated. Purification of the residue by chromatography (SiO$_2$, dichloromethane:methanol=30:1 to 15:1:) afforded the title compound (18 mg, 29%) as a white solid. MS: m/e=382.4 [M+H]$^+$.

The invention claimed is:

1. A method of treating Alzheimer's disease comprising administering a therapeutically effective amount of a substituted imidazo[1,5-a][1,2,4]triazolo[1,5-d][1,4]benzodiazepine of formula I

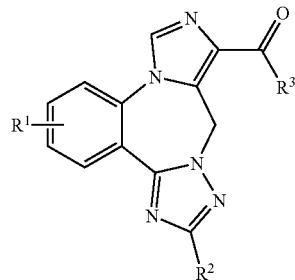

wherein
R$^1$ is halogen, lower alkyl, lower alkynyl, cycloalkyl, lower alkoxy, OCF$_3$, —NHR, —NHC(O)R or —NHSO$_2$R;
R$^2$ is hydrogen, methyl or aryl which is unsubstituted or substituted by one or two substituents selected from the group consisting of halogen and lower alkoxy; and
R$^3$ is lower alkyl;
or a pharmaceutically acceptable acid addition salt thereof.

2. The method of claim 1, wherein the compound is selected from the group consisting of
1-[3-fluoro-9H-imidazo[1,5-a][1,2,4]triazolo[1,5-d][1,4]benzodiazepin-10-yl]-ethanone,
1-[3-fluoro-9H-imidazo[1,5-a][1,2,4]triazolo[1,5-d][1,4]benzodiazepin-10-yl]-propan-1-one,
1-[3-Chloro-9H-imidazo[1,5-a][1,2,4]triazolo[1,5-d][1,4]benzodiazepin-10-yl]-propan-1 -one,
1-[3-bromo-9H-imidazo[1,5-a][1,2,4]thazolo[1,5-d][1,4]benzodiazepin-10-yl]-propan-1-one,
1-[3-bromo-9H-imidazo[1,5-a][1,2,4]thazolo[1,5-d][1,4]benzodiazepin-10-yl]-butan-1-one and
1-[3-bromo-9H-imidazo[1,5-a][1,2,4]thazolo[1,5-d][1,4]benzodiazepin-10-yl]-3-methyl-butan-1-one.

3. A compound of formula I-A

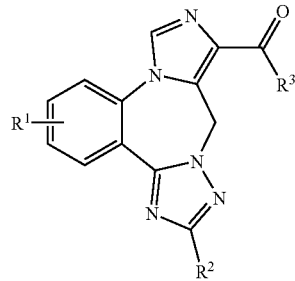

wherein
R$^1$ is halogen, lower alkyl, lower alkynyl, cycloalkyl, lower alkoxy, OCF$_3$, —NHR, —NHC(O)R or —NHSO$_2$R;
R$^2$ is hydrogen, methyl or aryl which is unsubstituted or substituted by one or two substituents selected from the group consisting of halogen and lower alkoxy; and
R$^3$ is lower alkyl;
or a pharmaceutically acceptable acid addition salt thereof.

4. The compound of claim 3, selected from the group consisting of
1-[3-bromo-9H-imidazo[1,5-a][1,2,4]triazolo[1,5-d][1,4]benzodiazepin-10-yl]-pentan-1-one,
1-[3-bromo-9H-imidazo[1,5-a][1,2,4]triazolo[1,5-d][1,4]benzodiazepin-10-yl]-ethanone.

5. The compound of claim 3, wherein $R^3$ is lower alkyl.

6. The compound of claim 5, selected from the group consisting of

1-[3-fluoro-9H-imidazo[1,5-a][1,2,4]triazolo[1,5-d][1,4]benzodiazepin-10-yl]-ethanone, 1-[3-fluoro-9H-imidazo[1,5-a][1,2,4]triazolo[1,5-d][1,4]benzodiazepin-10-yl]-propan-1-one, 1-[3-Chloro-9H-imidazo[1,5-a][1,2,4]triazolo[1,5-d][1,4]benzodiazepin-10-yl]-propan-1-one, 1-[3-bromo-9H-imidazo[1,5-a][1,2,4]triazolo[1,5-d][1,4]benzodiazepin-10-yl]-propan-1-one, 1-[3-bromo-9H-imidazo[1,5-a][1,2,4]triazolo[1,5-d][1,4]benzodiazepin-10-yl]-butan-1-one and 1-[3-bromo-9H-imidazo[1,5-a][1,2,4]triazolo[1,5-d][1,4]benzodiazepin-10-yl]-3-methyl-butan-1-one.

7. The compound of claim 3, wherein $R^1$ is halogen.

8. The compound of claim 3, wherein $R^1$ is cycloalkyl.

9. The compound of claim 3, wherein $R^2$ is hydrogen.

10. A composition comprising a therapeutically effective amount of compound of formula I-A

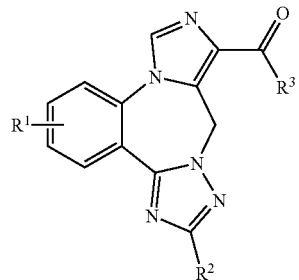

I-A wherein
$R^1$ is halogen, lower alkyl, lower alkynyl, cycloalkyl, lower alkoxy, $OCF_3$, —NHR, —NHC(O)R or —NHSO$_2$R;
$R^2$ is hydrogen, methyl or aryl which is unsubstituted or substituted by one or two substituents selected from the group consisting of halogen and lower alkoxy; and
$R^3$ is lower alkyl;

or a pharmaceutically acceptable acid addition salt thereof and a pharmaceutically acceptable carrier.

* * * * *